US008563609B2

(12) United States Patent
Miller

(10) Patent No.: US 8,563,609 B2
(45) Date of Patent: *Oct. 22, 2013

(54) NITRO FATTY ACIDS - NEUROPROTECTION AND/OR INHIBITION OF COGNITIVE DECLINE

(75) Inventor: Raymond A. Miller, Magnolia, OH (US)

(73) Assignee: Nitromega Corp., Pittsburgh, PA (US)

( * ) Notice: Subject to any disclaimer, the term of this patent is extended or adjusted under 35 U.S.C. 154(b) by 334 days.

This patent is subject to a terminal disclaimer.

(21) Appl. No.: 13/107,454

(22) Filed: May 13, 2011

(65) Prior Publication Data

US 2011/0280852 A1  Nov. 17, 2011

Related U.S. Application Data

(60) Provisional application No. 61/334,484, filed on May 13, 2010.

(51) Int. Cl.
| | | |
|---|---|---|
| A61K 31/202 | (2006.01) | |
| A61K 35/60 | (2006.01) | |
| A61K 36/00 | (2006.01) | |
| A61K 31/122 | (2006.01) | |

(52) U.S. Cl.
USPC ........... 514/558; 424/523; 424/725; 424/94.1

(58) Field of Classification Search
USPC .......................... 514/558; 424/523, 725, 94.1
See application file for complete search history.

(56) References Cited

U.S. PATENT DOCUMENTS

| | | | |
|---|---|---|---|
| 5,502,077 A | 3/1996 | Breivik et al. | |
| 5,656,667 A | 8/1997 | Breivik et al. | |
| 5,698,594 A | 12/1997 | Breivik et al. | |
| 6,245,811 B1 | 6/2001 | Horrobin et al. | |
| 6,579,866 B2 * | 6/2003 | McCleary | 514/188 |
| 6,652,879 B2 | 11/2003 | Opheim | |
| 6,924,309 B2 | 8/2005 | Ferrante et al. | |
| 7,312,191 B2 | 12/2007 | Rose et al. | |
| 7,645,795 B2 | 1/2010 | Kane et al. | |
| 7,776,916 B2 | 8/2010 | Freeman et al. | |

(Continued)

FOREIGN PATENT DOCUMENTS

| | | |
|---|---|---|
| WO | 0067596 | 11/2000 |
| WO | 0067596 A1 | 11/2000 |

(Continued)

OTHER PUBLICATIONS

Adjei et al. "A Phase I Trial of the Farnesyl Transferase Inhibitor SCH66336: Evidence for Biological and Clinical Activity"; 2000 American Association for Cancer Research; Cancer Res 2000;60:1871-1877.

(Continued)

*Primary Examiner* — Rosanne Kosson
(74) *Attorney, Agent, or Firm* — Dureska, Kennedy & Moore, L.L.C.; David P. Dureska; Brent L. Moore

(57) ABSTRACT

A composition for treating, ameliorating and/or preventing conditions associated with cognitive decline and/or motor neuron death comprise a fatty acid component enriched for one or more activated fatty acids and a nutraceutically acceptable excipient. A method for treating, ameliorating and/or preventing conditions associated with cognitive decline and/or motor neuron death includes administering a fatty acid component enriched for one or more activated fatty acids.

9 Claims, 3 Drawing Sheets

(56) References Cited

U.S. PATENT DOCUMENTS

| | | |
|---|---|---|
| 7,977,315 B2 | 7/2011 | Rose et al. |
| 2004/0006248 A1 | 1/2004 | Paiocchi et al. |
| 2004/0254240 A1 | 12/2004 | Ferrante et al. |
| 2005/0008690 A1 | 1/2005 | Miller |
| 2005/0222253 A1 | 10/2005 | Ferrante et al. |
| 2007/0232579 A1* | 10/2007 | Freeman et al. .............. 514/178 |
| 2009/0181974 A1 | 7/2009 | Bourgeade et al. |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082206 A1 | 4/2011 | Miller |
| 2011/0092594 A1 | 4/2011 | Yang |
| 2011/0105458 A1 | 5/2011 | Branchaud |
| 2011/0196037 A1 | 8/2011 | Yang |
| 2011/0319325 A1 | 12/2011 | Miller |

FOREIGN PATENT DOCUMENTS

| | | | |
|---|---|---|---|
| WO | 2005110396 A3 | 11/2005 | |
| WO | 2008153426 A1 | 12/2008 | |
| WO | 2009017802 A1 | 2/2009 | |
| WO | 2009129495 A1 | 10/2009 | |
| WO | 2009155439 A3 | 12/2009 | |
| WO | 2010014889 A3 | 2/2010 | |
| WO | 2010078504 A1 | 7/2010 | |
| WO | 2010129763 A1 | 11/2010 | |
| WO | 2010129777 A1 | 11/2010 | |
| WO | 2011014261 A1 | 2/2011 | |
| WO | 2011041639 A3 | 4/2011 | |
| WO | 2011152832 A1 | 12/2011 | |
| WO | 2012006014 A2 | 1/2012 | |

OTHER PUBLICATIONS

Artim et al. "Nitro-oleic acid targets transient potential (TRP) channels in capsaicin sensitive afferent nerves of rat urinary bladder"; Elsevier; Experimental Neurology 232 (2011) pp. 90-99.

Baker et al. "Red cell membrane and plasma linoleic acid nitration products: Synthesis, clinical identification, and quantitation"; PNAS Aug. 10, 2004; vol. 101, No. 32, pp. 11577-11582.

Baker et al. "Fatty Acid Transduction of Nitric Oxide Signaling; Multiple Nitrated Unsaturated Fatty Acid Derivatives Exist in Human Blood and Urin and Serve as Endogenous Peroxisome Proliferator-Activated Receptor Ligands"; The Journal of Biological Chemistry, vol. 280, No. 51, pp. 42464-42475, Dec. 23, 2005.

Baker et al. "Nitro-fatty Acid Reaction with Glutathione and Cysteine; Kinetic Analysis of Thiol Alkylation by a Michael Addition Reaction"; The Journal of Biological Chemistry, vol. 282, No. 42, pp. 31085-31093, Oct. 19, 2007.

Baker et al. "Convergence of nitric oxide and lipid signaling: Anti-inflammatory nitro-fatty acids"; Elsevier; Free Radical Biology & Medicine 46 (2009) pp. 989-1003.

Balazy et al. "Vicinal Nitrohydroxyeicosatrienoic Acids: Vasodilator Lipids Formed by Reaction of Nitrogen Dioxide with Arachidonic Acid"; The Journal of Pharmacology and Experimental Therapeutics; JPET 299: No. 2, pp. 611-619, 2001.

Balazy et al. "Trans-arachidonic acids: new mediators of nitro-oxidative stress"; Elsevier; Pharmacology & Therapeutics 119 (2008) pp. 275-290.

Bates et al. "Noncatalytic Interactions between Glutatione S-Transferases and Nitroalkene Fatty Acids Modulate Nitroalkene-Mediated Activation of Peroxisomal Proliferator-Activated Receptor •"; Biochemistry 2009, vol. 48; pp. 4159-4169.

Bates et al. "Nitroalkene Fatty Acids Mediate Activation of Nrf2/ARE-Dependent and PPAR•-Dependent Transcription by Distinct Signaling Pathways and with Significantly Different Potencies"; Biochemistry 2011, vol. 50; pp. 7765-7773.

Batthyany et al. "Reversible Post-translational Modification of Proteins by Nitrated Fatty Acids in Vivo"; The Journal of Biological Chemistry, vol. 281, No. 29, pp. 20450-20463, Jul. 21, 2006.

Bjorn "Clues emerge about benefits of briefly blocking blood flow"; Nature Medicine, vol. 15, No. 2, Feb. 2009.

Blanco et al. "6-Methylnitroarachidonate: A novel esterified nitroalkene that potently inhibits platelet aggregation and exerts cGMP-mediated vascular relaxation"; Elsevier; Free Radical Biology & Medicine 50 (2011) pp. 411-418.

Bloodsworth et al. "Nitric Oxide Regulation of Free Radical- and Enzyme-Mediated Lipid and Lipoprotein Oxidation"; Arteriosclerosis, Thrombosis, and Vascular Biology; Journal of the American Heart Association; 2000; 20: pp. 1707-1715.

Bonacci et al. "Gas-Phase Fragmentation Analysis of Nitro-Fatty Acids"; National Institute of Health; J Am Soc Mass Spectrum, Sep. 2011; 22(9); pp. 1534-1551.

Borniquel et al. "Nitrated oleic acid up-regulattes PPAR• and attenuates experimental inflammatory bowel disease"; Elsevier; Free Radical Biology & Medicine 48 (2010) pp. 499-505.

Boruwa et al. "Catalytic asymmetric Henry reaction"; Elsevier; ScienceDirect; Tetrahedron: Asymmetry 17 (2006) pp. 3315-3326.

Coffey et al. "Catalytic consumption of nitric oxide by 12/15-lipoxygenase: Inhibition of monocyte soluble guanylate cyclase activation"; PNAS, Jul. 3, 2001; vol. 98, No. 14; pp. 8006-8011.

Cole et al. "Nitro-Fatty Acid Inhibition of Neointima Formation After Endoluminal Vessel Injury"; American Heart Association; Circ Res. 2009; 105:965-972.

Coles et al. "Nitrolinoleate Inhibits Platelet Activation by Attenuating Calcium Mobilization and Inducing Phosphorylation of Vasodilator-stimulated Phosphoprotein through Elevation of cAMP*"; The Journal of Biological Chemistry; vol. 277, No. 8, Issue of Feb. 22, pp. 5832-5840; 2002.

Coles et al. "Nitrolinoleate Inhibits Superoxide Generation, Degranulation, and Integrin Expression by Human Neutrophils: Novel Antiinflammatory Properties of Nitric Oxide—Derived Reactive Species in Vascular Cells"; American Heart Association; Circ Res. 2002; 91:375-381; originally published online Aug. 1, 2002.

Cui et al. "Nitrated Fatty Acids; Endogenous Anti-inflammatory Signaling Mediators*"; The Journal of Biological Chemistry, vol. 281, No. 47, pp. 35686-35698, Nov. 24, 2006.

Davies et al. "Oxidized Alkyl Phospholipids Are Specific, High Affinity Peroxisome Proliferator-activated Receptor • Ligands and Agonists*"; The Journal of Biological Chemistry; vol. 276, No. 19, Issue of May 11, pp. 16015-16023, 2001.

Delerive et al. "Oxidized phospholipids activate PPAR• in a phospholipase A2-dependent manner"; 2000 Federation of European Biochemical Societies.

d'Ischia et al. "Medium-dependent Competitive Pathways in the Reactions of Polyunsaturated Fatty Acids with Nitric Oxide in the Presence of Oxygen". Structural Characterisation of Nitration Products and a Theoretical Insight; Elsevier; Tetrahendron 55 (1999) 9297-9308.

Easton et al. "Polyunsaturated Nitroalkanes and Nitro-Substituted Fatty Acids"; Synthesis 2001, No. 3, pp. 451-457.

Perricone Forever Young, Introducing the Metabolic Diet, Perricone 2010, Atria books, pp. 32-38.

Feelisch et al. "Concomitant S-, N-, and heme-nitros(yl)ation in biological tissues and fluids: implications for the fate of NO in vivo"; The FASEB Journal; vol. 16, Nov. 2002; pp. 1775-1785.

Ferreira et al. "Macrophage activation induces formation of the antiflammatory lipid cholesteryl-nitrolinoleate"; Biochemical Journal; 2009; 417, pp. 223-234.

Ferry et al. "Binding of prostaglandins to human PPAR•: tool assessment and new natural ligands"; Elsevier; European Journal of Pharmacology 417 (2001) pp. 77-89.

Freeman et al. "Nitro-fatty Acid Formation and Signaling*"; Journal of Biological Chemistry; Jun. 6, 2008; vol. 283; No. 283; pp. 15515-15519.

Gladwin et al. "The emerging biology of the nitrite anion"; Nature Chemical Biology; vol. 1; No. 6; Nov. 2005; pp. 308-314.

Henderer et al. Ocular Pharmacology; Section XIV Opthalmology, Chapter 63; pp. 1707-1711.

(56) References Cited

OTHER PUBLICATIONS

Gorczynski et al. "Regio- and Stereospecific Syntheses and Nitric Oxide Donor Properties of (D)-9- and (D)-10-Nitrooctadec-9-enoic Acids"; Department of Chemistry, Wake Forest University; Organic Letters 2006, vol. 8, No. 11, pp. 2305-2308.
Gorczynski et al. "Activation of peroxisome Proliferator-Activated Receptor • (PPAR•) by Nitroalkene Fatty Acids"; Importance of Nitration Position and Degree of Unsaturation; Journal Medicinal Chemistry 2009; 52, 4631-4639.
Groeger et al. "Signaling Actions of Electrophiles: Anti-inflammatory Therapeutic Candidates"; Department of Pharmacology & Chemical Biology, University of Pittsburgh, PA 15261; Feb. 2010, vol. 10; issue 1.
Guo et al. "Atypical PKCzeta transduces electrophilic fatty acid signaling in pulmonary epithelial cells"; Elsevier; Nitric Oxide 25 (2011) pp. 366-372.
Gutierrez et al. "Nitric Oxide Regulation of Superoxide-Dependent Lung Injury: Oxidant-Protective Actions of Endogenously Produced and Exogenously Administered Nitric Oxide"; Elsevier; Free Radical Biology & Medicine, vol. 21, No. 1, pp. 43-52, 1996.
Ichikawa et al. "Nitroalkenes Suppress Lipopolysaccharide-Induced Signal Transducer and Activator of Transcription Signaling in Macrophages: A Critical Role of Nitrogen-Activated Protein Kinase Phosphatase 1"; The Endocrine Society, Endocrinology 149(8):pp. 4086-4094, 2008.
Iles et al. "Fatty Acid Transduction of Nitric Oxide Signaling: Nitrolinoleic acid mediates protective effects through regulation of the ERK pathway"; National Institute of Health; Free Radic Biol Med. Apr. 1, 2009; 46(7): pp. 866-875.
Janero et al. "Differential nitros(yl)ation of blood and tissue constituents during glyceryl trinitrate biotransformation in vivo"; PNAS; vol. 101, No. 48; Nov. 30, 2004; pp. 16958-16963.
Kansanen et al. "Nrf2-dependent and -independent Responses to Nitro-fatty Acids in Human Endothelial Cells"; Journal of Biological Chemistry; vol. 284, No. 48, pp. 33233-33241, Nov. 27, 2009.
Karp et al. "Clinical and biologic activity of the farnesyltransferase inhibitor R115777 in adults with refractory and relapsed acute leukemias: a phase 1 clinical-laboratory correlative trial"; American Society of Hematology; 2001 97: pp. 3361-3369.
Kelley et al. "Nitro-oleic Acid, a Novel and Irreversible Inhibitor of Xanthine Oxidoreductase"; The Journal of Biological Chemistry, vol. 283, No. 52, pp. 36176-36184, Dec. 26, 2008.
Khoo et al. "Activation of Vascular Endothelial Nitric Oxide Synthase and Heme Oxygenases-1 Expression by Electrophilic Nitro-Fatty Acids"; National Institute of Health, Free Radic Biol Med. Jan. 15, 2010; 4892): 230.
Khoo et al. "Electrophilic Nitro-Fatty Acids: Anti-Inflammatory Mediators in the Vascular Compartment"; National Institute of Health, Curr Opin Pharmacol, Apr. 2010; 10(2); pp. 179-184.
Kissner et al. "Formation and Properties of Peroxynitrite as Studied by Laser Flash Photolysis, High-Pressure Stopped-Flow Technique, and Pulse Radiolysis"; American Chemical Society; Chem Res. Toxicol. 1997, 10, pp. 1285-1292.
Kliewer et al. "Fatty Acids and eicosanoids regulate gene expression through direct interactions with peroxisome proliferator-activated receptors a and •"; Proc. Natl. Acad. Sci. USA, vol. 94, pp. 4318-4323, Apr. 1997.
Koenitzer et al. "Redox signaling in inflammation: interactions of endogenous electrophiles and mitochondria in cardiovascular disease"; Ann. N.Y. Acad. Sci. 1203 (2010) pp. 45-52.
Larfars et al. "Activation of Nitric Oxide Release and Oxidative Metabolism by Leikotrienes B 4, C 4, and D 4 in Human Polymorphonuclear Leukocytes"; American Society of Hemotology; Blood 1999 93: pp. 1399-1405.
Lee et al. "Peroxisome proliferator-activated receptor-• in macrophage lipid homeostasis"; Elsevier; Trends in Endocrinology & Metabolism; vol. 13, No. 8, Oct. 2002; pp. 331-335.
Levy et al. "Lipid mediator class switching during acute inflammation: signals in resolution"; Nature Publishing Group; Nature Immunology, vol. 2, No. 7, pp. 612-619, Jul. 2001.
Lim et al. "Nitrolinoleate, a nitric oxide-derived mediator of cell function: Synthesis, characterization, and vasomotor activity"; PNAS, Dec. 10, 2002, vol. 99, No. 25, pp. 15941-15946.
Lima et al. "Characterization of Linoleic Acid Nitration in Human Blood Plasma by Mass Spectometry"; American Chemical Society; Biochemistry 2002, 41, pp. 10717-10722.
Liu et al. "Nitro-oleic acid protects the mouse kidney from ischemia and reperfusion injury"; Am J Physio Renal Physiol 295: F942-F949, 2008.
Liu et al. "Accelerated reaction of nitric oxide with O2 within the hydrophobic interior of biological membranes"; Biochemistry, Proc. Natl. Acad. Sci. USA, vol. 95, pp. 2175-2179, Mar. 1998.
Lundberg et al. "Nitrate and nitrite in biology, nutrition and therapeutics"; National Chemical Biology, vol. 5, No. 12, pp. 865-869, Dec. 2009.
Montuschi et al. "Isoprostanes: markers and mediators of oxidative stress"; The FASEB Journal, vol. 18, Dec. 2004, pp. 1791-1800.
Nadtochiy et al. "Mitochondrial nitroalkene formation and mild uncoupling in ischaemic preconditioning: implications for cardioprotection"; European Society of Cardiology, Cardiovascular Research (2009) 82, pp. 333-340.
Nadtocghiy et al. "Nitroalkenes Confer Acute Cardioprotection via Adenine Nucleotide Translocase 1"; Journal of Biological Chemistry, Jan. 27, 2012, vol. 287, No. 5, pp. 3573-3580.
Bernardi et al. "Zirconium Tetrachloride-Formaldehyde o-Complexes: A Computational and Spectroscopic Investigation"; The Journal of Organic Chemistry, vol. 65, No. 16, Aug. 11, 2000, pp. 4783-4790.
Napolitano et al. "The acid-promoted reaction of ethyl linoleate with nitrate. New insights from 15N-labelling and peculiar reactivity of a model skipped diene"; Elsevier, Tetrahedron 58 (2002) pp. 5061-5067.
Napolitano et al. "Acid-Induced Structural Modifications of Unsaturated Fatty Acids and Phenolic Olive Oil Constituents by Nitrite Ions: A Chemical Assessment"; American Chemical Society, Chem Res. Toxicol. 2004, 17, pp. 1329-1337.
O'Donnell et al. "Nitric Oxide Inhibition of Lipid Peroxidation: Kinetics of Reaction with Lipid Peroxyl Radicals and Comparison with α-Tocopherol"; American Chemical Society, Biochemistry 1997, 36, pp. 15216-15223.
O'Donnell et al. "Nitration of Unsaturated Fatty Acids by Nitric Oxide-Derived Reactive Nitrogen Species Peroxynitrite, Nitrous Acid, Nitrogen Dioxide, and Nitronium Ion"; American Chemical Society, Chem. Res. Toxicol. 1999, 12, pp. 83-92.
O'Donnell et al. "Catalytic Consumption of Nitric Oxide by Prostaglandin H Synthase-1 Regulates Platelet Function"; The Journal of Biological Chemistry, vol. 275, No. 49, Issue of Dec. 8, pp. 38239-38244, 2000.
O'Donnell et al. "Interactions Between Nitric Oxide and Lipid Oxidation Pathways: Implications for Vascular Disease"; Circulation Research, Journal of the American Heart Association, Circ Res. 2001; 88: 12-21.
O'Donnell et al. "15-Lipoxygenase Catalytically Consumes Nitric Oxide and Impairs Activation of Guanylate Cuclase"; The Journal of Biological Chemistry, vol. 274, No. 29, Issue of Jul. 16, pp. 20083-20091, 1999.
Pryor et al. "Reaction of Nitrogen Dioxide with Alkenes and Polyunsaturated Fatty Acids: Addition and Hydrogen Abstraction Mechanisms"; J. Am. Chem. Soc. 1982, 104, 6685-6692.
Quijano et al. "Reaction of Peroxynitrite with Mn-Superoxide Dismutase"; The Journal of Biological Chemistry, vo. 276, No. 15, Issue of Apr. 13, pp. 11631-11638, 2001.
Radi et al. "Peroxynitrite Oxidation of Sulfhydryls"; The Journal of Biological Chemistry, vol. 266, No. 7, Issue of Mar. 5, pp. 4244-4250, 1991.
Rubbo et al. "Nitric Oxide Regulation of Superoxide and Peroxynitrite-dependent Lipid Peroxidation"; The Journal of Biological Chemistry, vol. 269, No. 42, Issue of Oct. 21, pp. 26066-26075, 1994.
Rubbo et al. "Nitric Oxide Regulation of Tissue Free Radical Injury"; Chem. Res. Toxicol. 1996, 9, pp. 809-820.

(56) References Cited

OTHER PUBLICATIONS

Rubbo et al. "Nitric Oxide Reaction with Lipid Peroxyl Radicals Spares α-Tocopherol during Lipid Peroxidation"; The Journal of Biological Chemistry, vol. 275, No. 15, Issue of Apr. 14, pp. 10812-10818, 2000.

Rubbo et al. "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives"; Archives of Biochemistry and Biophysics, vol. 324, No. 1, Dec. 1, pp. 15-25, 1995.

Rudolph et al. "Cardiovascular Consequences When Nitric Oxide and Lipid Signaling Converge"; Circulation Research, Journal of the American Heart Association; Circ Res. 2009, 105: pp. 511-522.

Rudolph et al. "Nitro-Fatty Acids Reduce Atherosclerosis in Apolipoprotein E-Deficient Mice"; American Heart Association, Arteriosclerosis, Thrombosis, and Vascular Biology, 2010: 30: pp. 938-945.

Rudolph et al. "Endogenous generation and protective effects of nitro-fatty acids in a murine model of focal cardiac ischaemia and reperfusion"; European Society of Cardiology, Cardiovascular Research (1010) 85, pp. 155-166.

Rudolph et al. "Nitro-fatty Acid Metabolome: Saturation, Desaturation, B-Oxidation, and Protein Adduction"; Journal of Biological Chemistry, Jan. 16, 2009, vol. 284, No. 3, pp. 1461-1473.

Schopfer et al. "Fatty Acid Transduction of Nitric Oxide Signaling"; The Journal of Biological Chemistry, vol. 280, No. 19, Issue of May 13, pp. 19289-19297, 2005.

Schopfer et al. "Nitrolinoleic acid: An endogenous peroxisome proliferator-activated receptor • ligand"; PNAS, Feb. 15, 2005, vol. 102, No. 7, pp. 2340-2345.

Schopfer et al. "Detection and Quantification of Protein Adduction by Electrophilic Fatty Acids: Mitochondrial Generation of Fatty Acid Nitroalkene Derivatives"; Elsevier; National Institute of Health, Author Manuscript, Free Radic Biol Med. Jul. 27, 2011.

Schopfer et al. "Covalent Peroxisome Proliferator-activated Receptor • Adduction by Nitro-Fatty Acids"; The Journal of Biological Chemistry, vol. 285, No. 16, pp. 12321-12333, Apr. 16, 2010.

Sculptoreanu et al. "Nitro-Oleic Acid Inhibits Firing and Activates TRPV1- and TRPA1-Mediated Inward Currents in Dorsal Root Ganglion Neurons from Adult Male Rats"; The Journal of Pharmacology and Experimental Therapeutics, vo. 333, No. 3, pp. 883-895. 2010.

Shengming MA et al. "Hydrohalogenation Reaction of Substituted 1,2-Allenic Carboxylic Acids, Esters, Amides, Nitriles, and Diphenyl Phosphine Oxides"; Synthesis 2001, No. 5, Dec. 4, 2001.

Snider et al. "Oxidative and dehydrative cyclizations of nitroacetate esters with Mn(OAc)3"; Elsevier, Tetrahedron 58 (2002) pp. 7821-7827.

Tang et al. "Nitroalkenes induse rat aortic smooth muscle cell apoptosis via activation of caspase-dependent pathways"; Elsevier, Biochemical and Biophysical Research Communications 397, (2010) pp. 239-244.

Thatcher et al. "Nitrates and No Release: Contemporary Aspects in Biological and Medicinal Chemistry"; Elsevier, Free Radical Biology & Medicine, vol. 37, No. 8, pp. 1122-1143, 2004.

Thomas et al. "The biological lifetime of nitric oxide: Implications for the perivascular dynamics of NO and O2"; PNAS, Jan. 2, 2001, vol. 98, No. 1, pp. 355-360.

Villacorta et al. "Nitro-linoleic acid inhibits vascular smooth muscle cell proliferation via the Keap1/Nrf2 signaling pathway"; Am J Physio heart Circ Physiol 293: H770-H776, 2007.

Villacorta et al. "PPAR• and its ligands: therapeutic implications in cardiovascular disease"; Clinical Science (2009) 116, pp. 205-218.

Wang et al. "Effects of Endogenous PPAR Agonist Nitro-Oleic Acid on Metabolic Syndrome in Obese Zucker Rats"; Hindawi Publishing Corporation, PPAR Research, vol. 2010, Article ID 601562, 7 pages.

Wang et al. "Nitro-oleic acid protects against endotoxin-induced endotoxemia and multiorgan injury in mice"; Am J. Physio Renal Physiol 298: F754-F762, 2010.

Woodcock et al. "Synthesis of Nitrolipids. All Four Possible Diastereomers of Nitrooleic Acids: (E)- and (Z)-, 9- and 10-Nitro-octadec-9-enoic Acids;" American Chemical Society 2006, Organic Letters , vol. 8, No. 18, pp. 3931-3934.

Wright et al. "Fatty acid transduction of nitric oxide signaling: Nitrolinoleic acid potently activates endothelial heme oxygenase 1 expression"; PNAS, Mar. 14, 2006, vol. 103, No. 11, pp. 4299-4304.

Wright et al. "Human haem oxygenase-1 induction by nitro-linoleic acid is mediated by cAMP, AP-1, and E-box response element interactions"; Biochem. J. (2009) 422, pp. 353-361.

Zhang et al. "Nitro-Oleic Acid Inhibits Angiotensin II-Induced Hypertension"; 2010 American Heart Association, Circulation Research, Aug. 20, 2010.

Ono et al. A Convenient Procedure for the Conversion of (E)-Nitroalkenes to (Z)-Nitroalkenes via erythro-β- Nitroselenides J. Chem. Soc., Chem. Commun. 1987, 1551.

Sharpless et al. Am. Chem. Soc. 1973, 95:2697-2699.

Gallon & Pryor, "The Reaction of Low Levels of NitrogenDioxide with Methyl Linoleate in the Presence and Absence of Oxygen" Lipids1994, vol. 29, p. 171-176.

Gallon & Pryor, "The Identification of the Allylic Nitrite and Nitro Derivatives of Methyl Linoleate and Methyl Linolenate by Negative Chemical Ionization Mass Spectroscopy" Lipids 1993, vol. 28(2), p. 125-133.

Grisham, "Myoglobin-Catalyzed Hydrogen Peroxide Dependent Arachidonic Acid Peroxidation" Free Radic. Biol. Med. 1985, vol. 1, p. 227-232.

Kobayshi, "The Reaction of Nitrogen Dioxide With Lung Surface Components: The Reaction with cis-9- Octadecenoic Acid" Chemosphere 1983, vol. 12(9/10), p. 1317-1325.

Rudolph, et al., "Transduction of Redox Signaling by Electrophile-Protein Reactions", Science Signaling 2009, vol. 2, Issue 90 re7,p. 1-13.

Ferreira, et al., Nitroalkenes: synthesis, characterization, and effects on macrophage activation:, 2008, Methods Ensymo1441, p. 33-51.

Ichikawa et al. Nitroalkenes Suppress Lipopolysaccharide-Induced Signal Transducer and Activator of Transcription Signaling in Macrophages: A Critical Role of Mitogen-Activated Protein Kinase Phosphatase 1. Endocrinology, 2008, vol. 149(8), pp. 4086-4094; Abstract; p. 4089—para 1 http://endo.endojournals.org/content/149/8/4086.full.pdf.

* cited by examiner

NITRO FATTY ACIDS - NEUROPROTECTION AND/OR INHIBITION OF COGNITIVE DECLINE

This application claims the benefit of U.S. Provisional Application No. 61/334,484, filed May 13, 2010, which is hereby incorporated by reference in its entirety.

BACKGROUND OF THE INVENTION

Cognitive decline, such as memory loss, confusion, impaired judgment, personality changes, disorientation, and loss of language skills occurs in much of the population as they age, in varying degree. The most common, severe and irreversible form of cognitive decline is Alzheimer's disease, which, at present, is always fatal.

The symptoms of cognitive decline and Alzheimer's disease are thought to stem from the formation of amyloid plaques and neurofibrillary tangles, which are thought to contribute to the degradation of the neurons (nerve cells) in the brain and the subsequent onset of symptoms. Amyloid is a general term for protein fragments that the body produces normally. Beta-amyloid is a fragment of a protein that is snipped from another protein called amyloid precursor protein (APP). In a healthy brain, beta-amyloid protein fragments are broken down and eliminated. In individuals with Alzheimer's disease and other forms of cognitive decline, the fragments accumulate to form hard, insoluble plaques. Neurofibrillary tangles are insoluble twisted fibers that are found inside of the brain's cells. The protein contained in neurofibrillary tangles, i.e., the tau protein, forms a microtubule, which helps transport nutrients and other important substances from one part of the nerve cell to another. In Alzheimer's disease the tau protein is abnormal and the microtubule structures collapse.

Recent studies have shown that DHA can improve memory function. The memory Improvement seen with Docosahexaenoic acid (DHA) Study (MIDAS) published in *Alzheimer's & Dementia: The Journal of the Alzheimer's Association* showed that algal DHA improved memory function in healthy aging adults, providing a benefit roughly equivalent to having the learning and memory skills of someone three years younger. MIDAS was a large, randomized and placebo-controlled study demonstrating the benefits of DHA in maintaining and improving brain health in older adults. The goal of MIDAS was to evaluate the effects of algal DHA on cognitive outcomes in healthy elderly people with a mild memory complaint. The study funded by Martek Biosciences. MIDAS found that healthy people with memory complaints who took 900 mg algals DHA capsules for six months had almost double the reduction in errors on test that measure learning and memory performance versus those who took a placebo, a benefit roughly equivalent to having the learning and memory skills of someone three years younger. The DHA was well-tolerated and subjects taking the DHA also experienced a lower heart rate, providing a significant cardiovascular benefit. The study population included 484 people 55 and older at 19 U.S. sites who were considered to have age-related cognitive decline. Age-related cognitive decline is defined as decline in cognitive functioning consequent to the aging process that is within normal limits given a person's age. For example, individuals may report problems remembering names or appointments or may experience difficulty solving complex problems. MIDAS study participants consumed an oral dose of 900 mgs per day of algal. DHA or a placebo (corn/soy) over the course of six months. The primary endpoint was a cognitive test of memory and learning called the CANTAB Paired Associate Learning (PAL). CANTAB PAL is an assessment of visual memory and new learning, and is a useful tool for assessing patients with age-related memory loss.

SUMMARY OF THE INVENTION

The present invention is directed at the selection, formulation, and use of compositions and methods of treatment for conditions associated with cognitive decline and/or motor neuron death.

An embodiment of the present invention provides effective compositions of a fatty acid component enriched for one or more activated fatty acids to treat, ameliorate and/or prevent conditions associated with cognitive decline.

An alternative embodiment of the present invention provides methods for treating, ameliorating and/or preventing conditions associated with cognitive decline that comprise administering a fatty acid component enriched for one or more activated fatty acids.

Yet another embodiment of the present invention provides effective compositions of a fatty acid component enriched for one or more activated fatty acids to treat, ameliorate and/or prevent conditions associated with motor neuron death.

A further embodiment of the present invention provides methods for treating, ameliorating and/or preventing conditions associated with motor neuron death that comprise administering a fatty acid component enriched for one or more activated fatty acids.

DESCRIPTION OF DRAWINGS

For a fuller understanding of the nature and advantages of the present invention, reference should be made to the following detailed description taken in connection with the accompanying drawings, in which.

DETAILED DESCRIPTION OF THE INVENTION

Figure 1A:
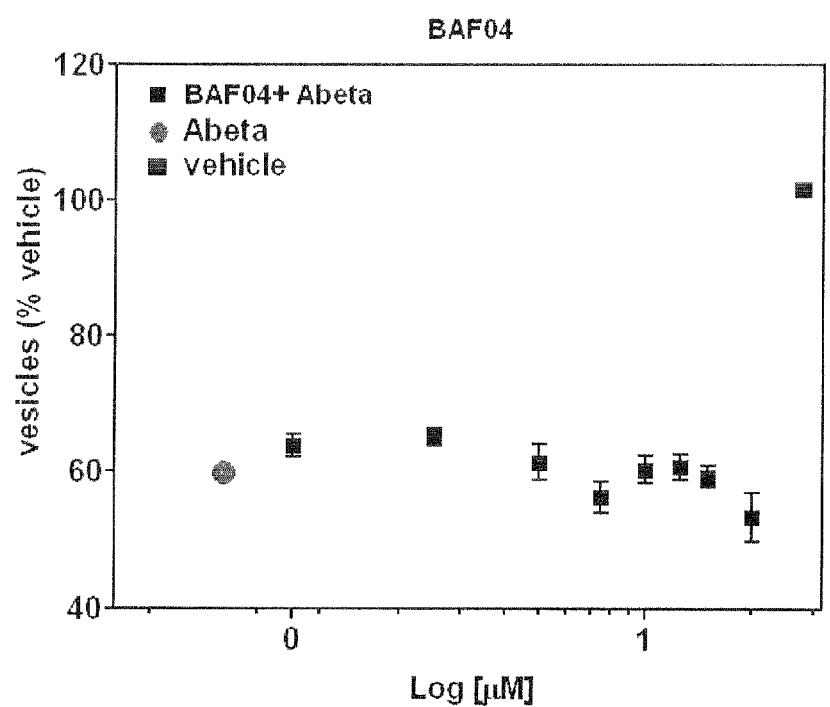
FIG. 1A shows a plot of exemplary data from an exocytosis assay performed on mature primary neuronal cultures grown for 3 weeks in vitro and shows a dose-dependent decrease in amyloid beta (Abeta) in intracellular vesicles resulting from administration of oleic acid.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer an agent to a patient, whereby the agent positively impacts the tissue to which it is targeted. Thus, as used herein, the term "administering", when used in conjunction with a nitrated lipid can include, but is not limited to, providing a nitrated lipid to a subject systemically by, for example, intravenous injection, whereby the agent reaches the target tissue. "Administering" a composition may be accomplished by, for example, injection, oral administration, topical administration, or by these methods in combination with other known techniques. Such combination techniques include heating, radiation, ultrasound and the use of delivery agents.

The term "animal" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

"Nutraceutical" as used herein generally refer to natural, bioactive chemical compounds that provide physiological benefits, including, disease prevention and health promotion, which may be used to supplement the diet. Nutraceuticals can be either purified or concentrated by using bioengineering methods and can be enhanced through genetic methods, which contain elevated levels of natural substances. Examples of nutraceuticals include isolated nutrients and herbal products and generally contain at least one of the following ingredients: a vitamin, a mineral, an herb or other botanical, an amino acid, a metabolite, constituent, extract, or combination of these ingredients. Common examples of nutraceuticals include beta-carotene, ephedra, ginko biloba, goldenseal, valerian, ginseng, green tea extract, and echinacea. The nutraceuticals described herein may be useful for maintenance and support of, for example, healthy joints, skin, eye and brain function, heart and circulatory system, and general health.

As used herein, the term "agent," "active agent," "therapeutic agent" or "therapeutic" means a compound or composition utilized to treat, combat, ameliorate, prevent or improve an unwanted condition or disease of a patient. In part, embodiments of the present invention are directed to affecting of inflammation, obesity, obesity-related diseases; metabolic diseases, cardiovascular and heart related diseases, cerebrovascular and neurodegenerative diseases, cognitive disorders, cancer or the aberrant proliferation of cells, and the like.

A "therapeutically effective amount" or "effective amount" of a composition is a predetermined amount calculated to achieve the desired effect, i.e., to inhibit, block, or reverse the activation, migration, or proliferation of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein and in the attached claims, the term "enriched" shall mean that the composition or portion of the composition includes a concentration of the identified component that is greater than the amount of the component naturally occurring in the composition. For example, with reference to activated fatty acids a composition enriched for activated fatty acids may include greater than at least 50 nM activated fatty acids. Therefore, a composition that is enriched for activated fatty acids may be at least 0.05% by weight activated fatty acid, at least 0.1% by weight activated fatty acid, at least 0.15% by weight activated fatty acid, at least 0.25% by weight activated fatty acid, at least 0.5% by weight activated fatty acid, at least 1.0% by weight activated fatty acid, at least 2% by weight activated fatty acid, and so on.

Modified fatty acids modified in accordance with the present invention are central nervous system drug candidates for the treatment of nervous system disorders with underlying inflammation, more particularly, Amyotrophic lateral sclerosis (ALS) are provided. Methods of treating, inhibiting, and/or abatement of inflammation and ALS with a derivative of fatty acids are also provided.

Modified fatty acids have been shown to be able to cross the blood brain barrier making them suitable candidates for the treatment of central nervous system disorders.

ALS, is a form of motor neuron disease caused by the degeneration of neurons located in the ventral horn of the spinal cord and the cortical neurons that provide their afferent input. ALS is characterized by rapidly progressive weakness, muscle atrophy and fasciculations, spasticity, dysarthria, dysphagia, and respiratory compromise. This disease is ultimately fatal primarily due to respiratory failure or complications with pneumonia within two to three years. Cognitive function is generally spared for most patients although a small subset of patients experience dementia.

The defining feature of ALS is the death of both upper and lower motor neurons in the motor cortex of the brain, the brain stem, and the spinal cord. Prior to their destruction, motor neurons develop proteinaceous inclusions in their cell bodies and axons. These inclusions often contain ubiquitin, and generally incorporate one of the ALS-associated proteins: superoxide dismutase (SOD1), TAR DNA binding protein (TDP-43, or TARDBP), or FUS.

The cause of ALS is not known, though an important step toward determining the cause came in 1993 when scientists discovered that mutations in the gene that produces the Cu/Zn superoxide dismutase (SOD1) enzyme were associated with some cases (approximately 20%) of familial ALS. This enzyme is a powerful antioxidant that protects the body from damage caused by superoxide, a toxic free radical generated in the mitochondria. Free radicals are highly reactive molecules produced by cells during normal metabolism again largely by the mitochondria. Free radicals can accumulate and cause damage to both mitochondrial and nuclear DNA and proteins within cells. To date, over 110 different mutations in SOD1 have been linked with the disease. Elevated levels of free radicals in neuronal cells can give rise to DNA and other cellular damage as well as induce an inflammatory state in the cells.

Nitro fatty acids may be able to play a role in the protecting motor neurons from damage induced by increased free radical levels in patients with SOD1 mutations. Nitrated linoleic acid ($LNO_2$) has been shown to display robust cell signaling activities that are generally anti-inflammatory in nature. Synthetic $LNO_2$ can inhibit human platelet function via cAMP-dependent mechanisms and inhibits neutrophil $O_2^-$ generation, calcium influx, elastase release, CD11b expression and degranulation via non-cAMP, non-cGMP-dependent mechanisms. $LNO_2$ may also induce vessel relaxation in part via cGMP-dependent mechanisms. In aggregate, these data, derived from a synthetic fatty acid infer that nitro derivatives of fatty acids represent a novel class of lipid-derived signaling mediators.

According to another embodiment, the invention comprises a method of inhibiting, treating, or abatement of neuronal inflammation, motor neuron disease or ALS in a mammal, the method comprising administering a derivative of a fatty acid or an activated fatty acid such as $NO_2$—OA. According to the method, the symptoms of motor neuron disease are one or more of muscle fasciculation (twitching), cramping, or stiffness of affected muscles; muscle weakness affecting an arm or a leg; slurred and nasal speech (dysarthria), difficulty moving, swallowing (dysphagia), tight and stiff muscles (spasticity), exaggerated reflexes (hyperreflexia) including an overactive gag reflex, An abnormal reflex (Babinski's sign) indicateing upper motor neuron damage, muscle atrophy, muscle cramps, and pseudobulbar affect, also known as "emotional lability", which consists of uncontrollable laughter, crying or smiling.

According to a preferred embodiment of the method, the inhibiting, treating, or abatement of neuronal inflammation, motor neuron disease or ALS comprises one or more of a reduction in inflammation; and/or inhibiting, treating, or abatement of one or both of free radical formation and neurodegeneration. Also according to a preferred embodiment of the method, inhibiting, treating, or abatement of neuronal cell death comprises inhibiting, treating, or abatement of one or more of neuronal cell inflammation and free radical formation and effects.

Fatty acids modified in accordance with the present invention are central nervous system drug candidates for the treatment of inflammatory conditions such as Guillain-Barré syndrome, vitamin deficiency, infectious diseases such as leprosy or shingles, or poisoning by toxins such as heavy metals. Many autoimmune pathologies also result in inflammation within the central nervous system Modified fatty acids are suitable candidates for the treatment of inflammatory conditions of the central nervous system due to their ability to cross the blood brain barrier and also due to their ability to as potent signaling mediators of inflammation. Recent research suggests that modified fatty acids are able to down regulate inflammation in mammalian tissues and cells including the central nervous system. Treatment with modified fatty acid preparations may have an important role in preventing the irreversible neuronal damage that results from uncontrolled inflammation within the central nervous system.

According to a preferred embodiment of the method, the inhibiting, treating, or abatement of neuronal inflammation, comprises one or more of a reduction in inflammation; and/or inhibiting, treating, or abatement of one or both of free radical formation and free radicals.

Modified fatty acids for the treatment of cognitive decline and motor neurone death can be combined with additional ingredients which enhance and complement modified fatty acid pharmacology.

Preferred embodiments include daily regimens of modified fatty acids and one or more of the following vitamins and minerals: Vitamin B12 (up to 25 mg daily, sublingual or administered intramuscularly), Vitamin E (Gamma E Tocopherol/Tocotrienols one to two soft gel caps per day with food), Zinc (15 mg daily), Copper (1 mg). There is evidence that copper is particularly beneficial in patients with ALS.

Further embodiments include daily regimens of modified fattys, vitamins and minerals and one or more of the following herbal supplements: Ginseng (400 mg daily) and *Ginkgo biloba* (standardized Extract, one capsule per day).

In yet further embodiments, daily regimens include modified fatty acids, vitamins and minerals, herbal supplements and other dietary supplements including: Amino acids (three tablespoons daily of Amino Fuel), Conenzyme Q10 (1200 mg daily), Creatine (micronized Creatine, two to four capsules per day with or without food), DHEA (15 mg to 75 mg), Glutathione (L-Glutathione, L-Cysteine and C, one capsule one to three times per day before food), N-Acetyl Cysteine (one capsule one to three times per day), Alpha-lipoic acid (R-dihydro-lipoic acid liquid caps, one to two capsules per day), Acetyl-L-Carnitine (L-carnitine, one to four capsules per day on an empty stomach with water or juice), Mega Green Tea Extract (one capsule per day with or without food), Resveratrol (20 mg daily), Selenium: (200 mcg daily), curcumin (900 mg), Mitochondrial Energy Optimizer (special antioxidant blend of R-dihydro-lipoic acid and acetyl-L-carnitine arginate and vinpocetine (5 mg daily).

These combinations can be customized to suit the particular needs and pre-existing medical conditions of a particular individual All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features.

As used herein, cognitive decline can be any change in an animal's cognitive function. For example cognitive decline, includes but is not limited to, memory loss (e.g. behavioral memory loss), failure to acquire new memories, confusion, impaired judgment, personality changes, disorientation, or any combination thereof. An agent that is effective to treat cognitive decline can also be effective for restoration of long term neuronal potentiation; inhibiting, treating, and/or abatement of neurodegeneration; inhibiting, treating, and/or abatement of general amyloidosis; inhibiting, treating, abatement of one or more of amyloid production, amyloid assembly, amyloid aggregation, amyloid oligomer binding, and amyloid deposition; inhibiting, treating, and/or abatement of the activity/effect of one or more of Abeta oligomers on a neuron cell; and any combination thereof. Cognitive decline also includes but is not limited to dementia, including but not limited to Alzheimer's Disease (AD), Down syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND), Frontotemporal dementia, Parkinson's Type (FTDP), progressive supranuclear palsy (PSP), Pick's Disease, Niemann-Pick's Disease, corticobasal degeneration, traumatic brain injury (TBI), dementia pugilistica, Creutzfeld-Jacob Disease and prion diseases; Cognitive Dysfunction in Schizophrenia (CDS); Mild Cognitive Impairment (MCI); Age-Associated Memory Impairment (AAMI); Age-Related Cognitive Decline (ARCD) or preclinical Alzheimer's disease (PCAD); Cognitive Impairment No Dementia (CIND); Addictions such as nicotine addiction; and the like.

A preferred embodiment of the present invention is to administer the compounds of the present invention to a patient in need thereof. The data would suggest that those diseases associated with oxidative damage would benefit preferentially. These diseases include, but are not limited to Alzheimer's Disease (AD), amyotrophic lateral sclerosis (ALS), motor neuron diseases (MND), traumatic brain injury (TBI), brain ischemia and the like.

As used herein an "activated fatty acid" refers to a fatty acid having at least one electron withdrawing group covalently bound to a carbon of the saturated or unsaturated aliphatic chain of a fatty acid. Such activated fatty acids may be substituted by any number of electron withdrawing groups at any number of positions on the hydrocarbon chain, and an electron withdrawing group may be positioned in either cis or trans configuration at a double bond or in either R or S absolute stereochemistry at an $sp^3$ chiral/stereogenic center. For example, in one embodiment, an activated fatty acid may have one electron withdrawing group, and in another, an activated fatty acid may be substituted with multiple electron withdrawing groups at multiple positions along the hydrocarbon chain. While the activated fatty acids of the invention may have an electron withdrawing group positioned at any carbon along the aliphatic hydrocarbon chain between the carboxy terminal carbon to the terminal methyl (ω), in some embodiments, the electron withdrawing group may be positioned within about 1 carbon from the carboxy terminal carbon and within about 1 carbon from the terminal methyl. In other embodiments, the electron withdrawing group may be positioned within about 3 carbons of either the carboxy terminal carbon and/or the methyl terminal carbon, and in still others embodiments, the electron withdrawing group may be positioned within 5 carbons of either of the carboxy terminal carbon and/or the methyl terminal carbon.

Nitration of fatty acids by $.NO_2$ can occur through several methods. For example, during both basal cell signaling and tissue inflammatory conditions, $.NO_2$ can react with membrane and lipoprotein lipids. In both in vivo and in vitro systems, $.NO_2$ has been shown to initiate radical chain autooxidation of polyunsaturated fatty acids via hydrogen abstraction from the bis-allylic carbon to form nitrous acid and a resonance-stabilized bis-allylic radical. Depending on the radical environment, the lipid radical species can react with molecular oxygen to form a peroxyl radical, which can react further to form lipid hydroperoxides then oxidized lipids. During inflammation or ischemic, when $O_2$ levels are lower, lipid radicals can react to an even greater extent with $.NO_2$ to generate multiple nitration products including singly nitrated, nitrohydroxy- and dinitro-fatty acid adducts. These products can be generated via hydrogen abstraction, direct addition of $.NO_2$ across the double bond, or both, and in some cases, such reactions may be followed by further reactions of the intermediate products that are formed. Hydrogen abstraction causes a rearrangement of the double bonds to form a conjugated diene; however, the addition of $.NO_2$ maintains a methylene-interrupted diene configuration to yield singly nitrated polyunsaturated fatty acids.

The reaction of polyunsaturated fatty acids with acidified nitrite ($HNO_2$) can generate a complex mixture of products similar to those formed by direct reaction with $.NO_2$, including the formation of singly nitrated products that maintain the bis-allylic bond arrangement. The acidification of $NO_2^-$ can create a labile species, $HNO_2$, which is in equilibrium with secondary products, including $N_2O_3$, $.NO$ and $.NO_2$, all of which can participate in nitration reactions. The relevance of this pathway as a mechanism of fatty acid nitration is exemplified by physiological and pathological conditions wherein $NO_2^-$ is exposed to low pH (e.g., <pH 4.0). This may conceivably occur in the gastric compartment, following endosomal or phagolysosomal acidification or in tissues following-post ischemic reperfusion.

Nitrated linoleic acid ($LNO_2$) has been shown to display robust cell signaling activities that are generally anti-inflammatory in nature. Synthetic $LNO_2$ can inhibit human platelet function via cAMP-dependent mechanisms and inhibits neutrophil $O_2^-$ generation, calcium influx, elastase release, CD11b expression and degranulation via non-cAMP, non-cGMP-dependent mechanisms. $LNO_2$ may also induce vessel relaxation in part via cGMP-dependent mechanisms. In aggregate, these data, derived from a synthetic fatty acid infer that nitro derivatives of fatty acids ($NO_2$—FA) represent a novel class of lipid-derived signaling mediators. To date, a gap in the clinical detection and structural characterization of nitrated fatty acids has limited defining $NO_2$—FA derivatives as biologically-relevant lipid signaling mediators that converge $.NO$ and oxygenated lipid signaling pathways.

In some embodiments, the nutraceutical supplements may include one or more nutraceutical other than nitro fatty acids such as one or more vitamins, on ore more unmodified fatty acids (e.g. EPA or DHA, preferably DHA) one or more minerals, plant extracts or oils, rice bran oil, enzyme-treated stabilized rice bran, a solubilized fraction of rice bran oil, and derivatives thereof, glucosamine derivatives, methylsulfonylmethane, yucca concentrate, grape seed extract, beta-carotene, ephedra, ginko biloba, goldenseal, valerian, ginseng, green tea extract, and echinacea. The activated fatty acids may be isolated from a natural source or prepared using fatty acids derived from a natural source such as fish oils or plant oils and may be derived from omega-3 fatty acids, omega-6 fatty acids, omega-9 fatty acids, linoleic acid, α-linoleic acid, oleic acid, eicosapentaenoic acid, docosahexaenoic acid or a derivative or combination thereof. In particular embodiment, the nutraceuticals may further include non-nitrated fatty acids, preferably DHA. In certain embodiments and for dietary and nutritional supplement embodiments, the nutraceutical may be provided as a gel capsule and, in particular embodiments, a flavored gel capsule. In some embodiments, the nutritional supplement may be an additive for food.

Some embodiments are directed to a dietary supplement including a fatty acid component enriched for one or more activated fatty acids and a nutraceutically acceptable excipient. In some embodiments, the activated fatty acid may be derived from an omega-3 fatty acid, an omega-6 fatty acid, an omega-9 fatty acid, and combinations thereof. In other embodiments, the activated fatty acid may be a nitro-fatty acid or a keto-fatty acid, and in particular embodiments, the activated fatty acid may be nitro-linoleic acid, nitro-α-linoleic acid, nitro-γ-linoleic acid, nitro-oleic acid, nitro-eicosapentaenoic acid, nitro-docosahexaenoic acid, conjugated nitrolinoleic acid, such as octadeca-9-nitro-9-cis-1-trans dienoic acid, keto-linoleic acid, keto-α-linoleic acid, keto-γ-linoleic acid, keto-oleic acid, keto-eicosapentaenoic acid, keto-docosahexaenoic acid or a derivative or combination thereof. In still other embodiments, the dietary supplement may also include one or more of linoleic acid, α-linoleic acid, γ-linoleic acid, oleic acid, eicosapentaenoic acid (EPA), docosahexaenoic acid (DHA), or derivatives thereof DHA and/or nitratel DHA are preferable for cognitive disorders. In some embodiment, the dietary supplement may further include one or more nutraceutical selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof.

In certain embodiments, the dietary supplement may be a gel capsule, and in some embodiments, the one or more activated fatty acids may be about 5% by weight to about 95% by weight of the total gel capsule.

In particular embodiments, the dietary supplement may include a first fatty acid component enriched for one or more: activated fatty acid selected from nitro-linoleic acid, keto-linoleic acid, nitro-oleic acid, and keto-oleic acid and a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof, and in some embodiments, the dietary supplement may further include vitamin F or a derivative thereof. In other embodiments, the dietary supplement may include one or more secondary agent including but not limited to vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, gugulipids, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote cognitive health or formulated as a neuroprotectant.

Other embodiments are directed to a gel capsule including a core having a fatty acid component enriched for one or more activated fatty acids and one or more coating layers encapsulating the core. In some embodiments, the gel capsule may be flavored, and in particular embodiments, the flavoring agent may be a flavor selected from berry, strawberry, chocolate, cocoa, lemon, butter, almond, cashew, macadamia nut, coconut, blueberry, blackberry, raspberry, peach, lemon, lime, mint, orange, banana, chili pepper, pepper, cinnamon, and pineapple. In some embodiments, at least one of the one or more coating layers may include at least one flavoring agent, and in other embodiments, the core may include at least one flavoring agent. In further embodiments, at least one of the one or more coating layers may be an enteric coating, and in still further embodiments, the core may further include one or more agents selected from solubilizers, stabilizers, colorants, plastizers diluents, fillers, disintegrants, binders, lubricants, surfactants, hydrophobic vehicles, water soluble vehicles, emulsifiers, buffers, humectants, moisturizers, antioxidants, or preservatives. In some embodiments, the core, at least one of the one or more coating layers, or a combination thereof further comprises one or more secondary agents.

In certain embodiments, such gel capsules may be formulated to include a core having from about 10 mg to about 500 mg of one or more activated fatty acid and from about 10 mg to about 100 mg of vitamin C and one or more coating layers encapsulating the core, and the core, at least one of the one or more coating layers, or combinations thereof may include from about 0.25% by weight to about 3.0% by weight of one or more flavoring agents. In other embodiments, such gel capsules may be formulated to include a core having from about 10 mg to about 500 mg of one or more activated fatty acid and from about 2 mg to about 50 mg of vitamin E and one or more coating layers encapsulating the core, and the core, at least one of the one or more coating layers, or combinations thereof may include from about 0.25% by weight to about 3.0% by weight of one or more flavoring agents.

Still other embodiments are directed to a method for preparing a gel capsule including the steps of combining gelswatch ingredients, melting the gelswatch ingredients to form a liquefied gelswatch, combining the liquefied gelswatch with a fatty acid component that is enriched for one or more activated fatty acids, and encapsulating the fatty acid component to form a gel capsule. In some embodiments, the method may further include drying the gel capsule, washing the gel capsule, and packaging the gel capsules. In certain embodiments, the gelswatch ingredients may include, for example, gelatin or a gelatin substitute, modified starch or other suitable gelatin substitute, a softener, glycerol, sorbitol or other suitable polyol, a flavoring agent, a coloring agent, keratin and combinations thereof.

Further embodiments are directed to methods for improving the health of an individual by administering to the individual a dietary supplement including a fatty acid component enriched for one or more activated fatty acids, and a nutraceutically acceptable excipient. In some embodiments, the dietary supplement may include a first fatty acid component enriched for one or more activated fatty acid selected from nitro-linoleic acid, keto-linoleic acid, nitro-oleic acid, and keto-oleic acid and a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof, and in particular embodiments, the dietary supplement may further include vitamin E or a derivative thereof. In some embodiments, the dietary supplement may further include one or more secondary agent selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, guggulipds, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote cognitive health or formulated as a neuroprotectant.

Various embodiments of the invention are also directed to compositions including a core having one or more nitro fatty acids and one or more coating layers encapsulating the core. In such embodiments, the one or more nitro fatty acids may make up about 10% by weight to about 95% by weight of the total gel capsule. As above, the compositions may include one or more additional secondary components such as, for example, rice bran oil, enzyme-treated stabilized rice bran, a solubilized fraction of rice bran oil, and derivatives thereof, glucosamine derivatives, methylsulfonylmethane, yucca concentrate, grape seed extract, beta-carotene, ephedra, ginko biloba, goldenseal, valerian, ginseng, green tea extract, and echinacea. The activated fatty acid may be derived from omega-3 fatty acids, omega-6 fatty acids, omega-9 fatty acids, linoleic acid, α-linoleic acide, oleic acid, eicosapentaenoic acid, docosahexaenoic acid or a derivative or combination thereof, and may contain non-activated fatty acids.

Such compositions may be gel capsules, and such gel capsules may be flavored by providing one or more coating layers with at least one flavoring agent and/or the core with at least one flavoring agent. The flavoring agent may vary among embodiments and may be selected from berry, strawberry, chocolate, cocoa, lemon, butter, almond, cashew, macadamia nut, coconut, blueberry, blackberry, raspberry, peach, lemon, lime, mint, orange, banana, chili pepper, pepper, cinnamon, and pineapple, and in some embodiments, the gel capsule may include an enteric coating. The core may further include other agents such as solubilizers, stabilizers, colorants, plasticizers diluents, fillers, disintegrants, binders, lubricants, surfactants, hydrophobic vehicles, water soluble vehicles, emulsifiers, buffers, humectants, moisturizers, antioxidants, preservatives or combinations thereof.

In still other embodiments, the core, at least one of the one or more coating layers, or a combination thereof may further include one or more secondary agents such as, for example, antioxidants, statins, squalene synthesis inhibitors, azetidinone-based compounds, low-density lipoprotein (LDL) catabolism activators, peroxisome proliferator-activated receptor (PPAR) antagonists or agonists, antiarrhythmic agent, non-steroidal anti-inflammatory drugs (NSAIDs) and nutraceutical equivalents thereof.

Embodiments of the invention also include methods for preparing a nitro-fatty acid by isolating nitro fatty acids from fish oils or plant oils, and methods for preparing a gel capsule by combining gelswatch ingredients; melting the gelswatch ingredients to form a liquefied gelswatch; combining the liquefied gelswatch with the nitro fatty acid; encapsulating the nitro fatty acid to form a gel capsule; drying the gel capsule; washing the gel capsule; and packaging the gel capsules.

Other methods for preparing a nitro fatty acid include the steps of contacting an existing unsaturated fatty acid composition with a nitro containing compound and reacting the existing unsaturated fatty acid with a nitro containing compound to form a nitro fatty acid. Methods for preparing a gel capsule including the steps of combining gelswatch ingredients, melting the gelswatch ingredients to form a liquefied gelswatch, combining the liquefied gelswatch with the nitro fatty acid, encapsulating the nitro fatty acid to form a gel capsule, drying the gel capsule, washing the gel capsule, and packaging the gel capsules.

Still other methods for preparing gel capsules including one or more activated fatty acid include the steps of contacting an unsaturated fatty acid with a mercuric salt and a selenium compound; contacting an intermediate resulting from step 1 with an electron withdrawing group donating reagent; reacting the intermediate resulting from step 2 with an oxidizing agent; combining gelswatch ingredients; melting the gelswatch ingredients to form a liquefied gelswatch; combining the liquefied gelswatch with the nitro fatty acid; encapsulating the nitro fatty acid to form a gel capsule; drying the gel capsule; washing the gel capsule; and packaging the gel capsules.

Yet other methods for preparing gel capsules including one or more activated fatty acid include the steps of combining a first component at least comprising an aliphatic hydrocarbon having an electron withdrawing group at one end and a second component at least comprising aliphatic hydrocarbon chain having an aldehyde at one end in the presence of a base to form a first intermediate; generating an alkene from the first intermediate; combining gelswatch ingredients; melting the gelswatch ingredients to form a liquefied gelswatch; combining the liquefied gelswatch with the nitro fatty acid; encapsulating the nitro fatty acid to form a gel capsule; drying the gel capsule; washing the gel capsule; and packaging the gel capsules.

Gelswatch ingredients may be selected from gelatin or a gelatin substitute, modified starch or other suitable gelatin substitute, a softener, glycerol, sorbitol or other suitable polyol, a flavoring agent, a coloring agent, keratin and combinations thereof.

In certain embodiments, the electron withdrawing group may be positioned on a carbon directly attached to a double bond of the activated fatty acid forming an "electron withdrawing vinyl" group. The electron withdrawing group of such vinyl groups may be on either side of the double bond. Fatty acids encompassed by embodiments of the invention may have one or more than one electron withdrawing vinyl groups at any carbon on the aliphatic hydrocarbon chain, and there are several ways that an unsaturated fatty acid can have one electron-withdrawing group. In one embodiment, an activated oleic acid (ocatadecac-9-enoic acid) which is an 18 carbon, ω-6 fatty acid with one double bond (denoted "18:1") between the $6^{th}$ (C-9) and $7^{th}$ (C-10) carbons, may have an electron withdrawing group at either C-9 or C-10. In another exemplary embodiment, an activated linoleic acid (octadeca-9,12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at C-9 or C-10 or C-12 or C-13. Similarly, other polyunsaturated fatty acids, with 3, 4, 5, 6 or more double bonds, can have one electron withdrawing at either position on any of the double bond carbons, including all possible permutations of positions and electron-withdrawing groups.

In other embodiments, a mono or polyunsaturated fatty acid may have two electron-withdrawing groups, and there are several ways that an unsaturated fatty acid can have two electron-withdrawing groups. For example, in one embodiment, an activated oleic acid (ocatadecac-9-enoic acid) which is an 18 carbon, ω-6 fatty acid with one double bond (denoted "18:1") between the $6^{th}$ (C-13) and $7^{th}$ (C-12) carbons, may have an electron withdrawing group at both C-13 and C-12. In another exemplary embodiment, an activated linoleic acid (octadeac-9,12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at any two of the positions C-9, C-10, C-12 or C-13, with the following possible permutations: C-9 and C-10, C-9 and C-12, C-9 and C-13, C-10 and C-12, C-10 and C-13, or C-12 and C-13. Similarly, other polyunsaturated fatty acids, with shorter or longer carbon chain lengths and 3, 4, 5, 6 or more double bonds, can have two electron withdrawing at two of the positions on any of the double bond carbons, including all possible permutations of positions and electron-withdrawing groups.

In analogy to the preceding descriptions of compounds with one electron-withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, can have multiple electron withdrawing (three, four, five or more, as available positions for substitution permit) at any of the positions on any of the double bond carbons, including all possible permutations of positions and electron-withdrawing groups.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ (σ[P]) is about −0.7 and the σ[P] for a nitro group is about 0.8.

Embodiments of the invention encompass any known electron withdrawing group. For example, electron-withdrawing groups may include, but are not limited to, aldehyde (—COIF), acyl (—COR), carbonyl (—CO), carboxylic acid (—COOH), ester (—COOR), halides (—Cl, —F, —Br, etc.), fluoromethyl cyano (—CN), sulfonyl sulfone (—$SO_2R$), sulfonic acid (—$SO_3H$), 1°, 2° and 3° ammonium (—$NR_3^+$), and nitro (—$NO_2$). In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl. In other embodiments, the activated fatty acids of the invention may be additionally substituted by non-electron withdrawing groups or electron donating groups including, for example, alcohol (—OH), reverse ester (—OOCR), alkyl, alkenyl, alkynyl, 1° and 2° amines (—$NR_2$), nitrate (—$ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include nitrated fatty acid having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons. Embodiments of the invention may encompass fatty acids having an odd number of carbons and/or a non-naturally occurring linker. Some embodiments of the invention include fatty acids having from 4 to 22 carbons, and others include fatty acids having from 12 to 18 carbons in the aliphatic hydrocarbon chain. In still other embodiments, fatty acids may have greater than 24 carbons in the aliphatic hydrocarbon chain. The fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitoalkene analog of a "cis" double bond is actually an E nitroalkene. Similarly, the nitoalkene analog of a "trans" double bond is actually a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated ratty acid may have, 4, 6, 8, 10, 12, 14, 16, 18, 20, 22 and so on carbons and may include omega($\omega$)-3, $\omega$-5, $\omega$-6, $\omega$-7, $\omega$-9 fatty acids and the like. Any such fatty acid may be useful in embodiments of the invention. The symbol '$\omega$' is used to refer to the terminal methyl carbon of the aliphatic hydrocarbon chain. The placement of the double bond of the w-X fatty acid is the carbon-carbon bond X number of carbons from the $\omega$ carbon. For example, an $\omega$-6 fatty acid has a double bond between the $6^{th}$ and $7^{th}$ carbons counting backward from the $\omega$ carbon and an $\omega$-3 fatty acid has a double bond between the $3^{rd}$ and $4^{th}$ carbons counting backward from the $\omega$ carbon. Various embodiments of the invention include nitrated $\omega$-3 fatty acids, including, but not limited to, linolenic acid, alpha-linolenic acid, eicosapentanoic acid, docosapentaenoic acid, docosahexanoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, palmitoleic acid; and nitrated $\omega$-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid. Embodiments of the invention also include synthetic equivalents to naturally occurring fatty acids and derivatives thereof.

In particular embodiments, the fatty acids utilized in embodiments of the invention may be omega-3 fatty acids. As used herein, the term "omega-3 fatty acids" or "$\omega$-3 fatty acids" may include natural or synthetic omega-3 fatty acids, or pharmaceutically acceptable esters, derivatives, conjugates (see, e.g., U.S. Publication No. 2004/0254357 to Zaloga et al. and U.S. Pat. No. 6,245,811 to Horrobin et al., each of which is hereby incorporated by reference in its entirety), precursors or salts thereof and mixtures thereof. Examples of $\omega$-3 fatty acid oils include but are not limited to $\omega$-3 polyunsaturated, long-chain fatty acids such as a cicosapentaenoic acid (EPA), docosahexaenoic acid (DHA), and $\alpha$-linolenic acid; esters of $\omega$-3 fatty acids with glycerol such as mono-, di- and triglycerides; and esters of the $\omega$-3 fatty acids and a primary, secondary or tertiary alcohol such as fatty acid methyl esters and fatty acid ethyl esters. In certain embodiments, the $\omega$-3 fatty acid oils may be long-chain fatty acids such as EPA or DHA, triglycerides thereof, ethyl esters thereof and mixtures thereof. For example, in some embodiments, the fatty acids may be esterified to more complex glycerolipids such as phospholipids, sphingolipids, glycolipids, or the like. The $\omega$-3 fatty acids or their esters, derivatives, conjugates, precursors, salts and mixtures thereof can be used either in their pure form or as a component of an oil, such as fish oil or plant oil, preferably purified fish oil or plant oil concentrates.

Various fish oils are known and useful as sources for $\omega$-3, $\omega$-6, and $\omega$-9 fatty acids, and any such oil may be used in embodiments of the invention. For example, oils derived from herring, sardines, mackerel, lake trout, flounder, albacore tuna, krill, and salmon are useful sources of $\omega$-3, $\omega$-6, and $\omega$-9 fatty acids. In other embodiments, commercially available $\omega$-3 fatty acids suitable for use in the invention may include, but are not limited to, Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, K85TG, K85EE, K80EE and EPAX7010EE (Pronova Biocare a.s., 1327 Lysaker, Norway). In certain embodiments, the $\omega$-3, $\omega$-6, and $\omega$-9 fatty acids may be a mixture of several $\omega$-3, $\omega$-6, and $\omega$-9 fatty acids such as OMACOR™ omega-3 fatty acids which are combinations of EPA and DHA $\omega$-3 fatty acids, and are described in U.S. Pat. Nos. 5,502,077, 5,656,667 and 5,698,594, which are hereby incorporated by reference in their entireties.

Other embodiments of the invention include unsaturated or polyunsaturated non-naturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups which interrupt the aliphatic hydrocarbon chain. For example, in some embodiments, activated fatty acids may have one or more non-carbon-carbon linkage such as, for example, ester, ether, vinyl ether, amino, imine and the like at any position within the aliphatic hydrocarbon chain.

For example, embodiments of the invention include compounds of general formulae I and II:

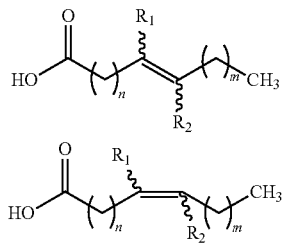

wherein $R_1$ and $R_2$ are independently selected from —H and any electron withdrawing groups including, but not limited to —COH, —COR, —CO, —COOH, —COOR, —Cl, —F, —Br, —I, —CF$_3$, —CN, —SO$_3^-$, —SO$_2$R, —SO$_3$H, —NH$_3^+$, —NH$_2$R$^+$, —NHR$_2^+$, —NR$_3^+$ and —NO$_2^-$ wherein at least one of $R_1$ and $R_2$ is an electron withdrawing group and m and n are, independently, 1-20. Some embodiments include compounds of general formula III:

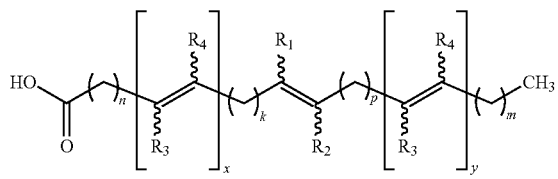

wherein $R_1$, $R_2$, m and n are as described above, $R_3$ and $R_4$ are, independently, selected from —H, —COH, —COR, —CO, —COOH, —COOR, —Cl, —F, —Br, —I, —CF$_3$, —CN, —SO$_3^-$, —SO$_2$R, —SO$_3$H, —NH$_3^+$, —NH$_2$R$^+$, —NHR$_2^+$, —NR$_3^+$ and —NO$_2^-$, k and p are, independently, 0 to 5 and x and y are independently, 0 to 3, and wherein each double bond is in either cis or trans configuration. In still other embodiments, any carbon associated with m, n, k or p may be substituted.

The activated fatty acids described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of activated fatty acids of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Suitable pharmaceutically acceptable base addition salts used in connection with the activated fatty acids of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Activated fatty acids as described in various embodiments of the invention above, may be administered to individuals to treat, ameliorate and/or prevent a number both acute and chronic conditions associated with cognitive decline.

The embodiments of the compositions of the present invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, ocular, intravaginally, or inhalation. In certain embodiments, the administration may be parenteral. In some embodiments, the nutraceutical may be prepared in the presence or absence of stabilizing additives that favors extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an activated fatty acid may be deposited to a site of injury or inflammation, such as, for example, the site of a surgical incision or a site of inflammation due to arthroscopy, angioplasty, stent placement, by-pass surgery and so on.

Various embodiments, of the invention are also directed to method for administering activated fatty acids. Specific modes of administration may vary and may depend on the indication. The selection of the specific route of administration and the dose regimen may be adjusted or titrated according to known methods in order to obtain the optimal response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art. Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix 11, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

In various embodiments, an effective amount of an activated fatty acid delivered during each administration cycle of the nutraceutical may range from about 10 mg/m$^2$/day to about 1000 mg/m$^2$/day. In some embodiments, an effective amount may be about 20 mg/m$^2$/day to about 700 mg/m$^2$/day, and in others, an effective amount may be about 30 mg/m$^2$/day to about 600 mg/m$^2$/day. In particular embodiments, an effective amount may be about 50 mg/m$^2$/day, about 400 mg/m$^2$/day, about 500 mg/m$^2$/day, or about 600 mg/m$^2$/day. In yet other embodiments, an effective amount of an activated fatty acid may vary as treatment progresses. For example, a dosage regimen may be increased or decreased as treatment proceeds through administration cycles, or the daily dosage may increase or decrease throughout administration. In additional embodiments, greater than 1000 mg/m$^2$/day may be administered because even high doses of activated fatty acid are generally tolerable to the patient and may not produce undesired physiological effects.

In some embodiments, activated fatty acids administered may include up at least 5% by weight, at least 10% by weight, at least 20% by weight, at least 30% by weight, at least 40% by weight, at least 50% by weight, at least 60% by weight at least 70% by weight, at least 80% by weight, at least 90% by weight or at least 100% by weight of one or more species of activated fatty acid. In particular embodiments, a single species of activated fatty acid may make up at least 10% by weight, at least 20% by weight, at least 30% by weight, at least 50%, at least 60% by weight, at least 70% by weight, at least 80% by weight of the total activated fatty acid administered, and in other embodiments, a single species of activated fatty acids may make up about 5% to about 100% by weight, about 25% to about 75% by weight, or about 40% to about 55% by weight of the fatty acids administered. In particular embodiments, the ratio of activated fatty acid to non-activated may be from about 99:1 to about 1:99, about 1:4 to about 4:1, about 1:3 to about 3:1 or about 1:2 to about 2:1.

For example, in some embodiments, the activated fatty acids may be prepared from one of EPA or DHA or a combination of EPA and DHA. It is preferred that the DHA or modified DHA (e.g. nitro modified DHA) exceed the amount of EPA in the formula. The composition administered may include about 5% to about 100% by weight, about 25% to about 75% by weight, or about 30% to about 60% by weight activated EPA and/or activated DHA, and any remainder may be made up of non-activated EPA and/or DHA. In compositions containing both activated EPA and activated DHA, the activated EPA and activated DHA may be present in a weight ratio of from 99:1 to 1:99, 1:4 to 4:1, 1:3 to 3:1, 1:2 to 2:1, or 1:1. In compositions containing activated EPA and/or activated DHA as well as non-activated EPA and/or DHA, the weight ratio of activated:non-activated may be from 99:1 to 1:99, 1:4 to 4:1, 1:3 to 3:1 or 1:2 to 2:1. In the embodiments described above, the percentage by weight may be based on the free acid or ester forms, although it is preferably based on the ethyl ester form of the ω-3 fatty acids even if other forms are utilized in accordance with the present invention.

In still other embodiments, the activated fatty acid may be prepared from a different base fatty acid than the non-activated fatty acids with which it is combined. For example, in some embodiments, the activated fatty acid may be an activated linoleic acid, an activated oleic acid, or combinations thereof, and these activated fatty acids may be combined with non-activated EPA and/or DHA. In such embodiments, the ratio of activated linoleic acid and/or activated oleic acid to non-activated EPA and/or DHA may be from about 99:1 to 1:99, 1:4 to 4:1, 1:3 to 3:1, 1:2 to 2:1, or 1:1. In particular embodiments, activated linoleic acid or oleic acid may be combined with EPA and DHA, and each of the three components may be provided in a ratio of from about 1:1:1, 2:1:1, 1:2:1, 1:1:2, 2:2:1, 1:2:2, 3:1:1, and the like.

In some embodiments, the dosage regimen as described above may be combined with a secondary form of treatment or a secondary agent. For example, activated fatty acids such as those described above may be combined with antioxidants, statins, squalene synthesis inhibitors, azetidinone-based compounds, low-density lipoprotein (LDL) catabolism activators, peroxisome proliferator-activated receptor (PPAR) antagonists or agonsits, antiarrhythmic agent, non-steroidal anti-inflammatory drugs (NSAIDs) and the like, and combinations thereof.

The antioxidants of various embodiments, may include any antioxidant known in the art such as tocopherols, oils, such as soybean oil and partially hydrogenated vegetable oil, and lubricants such as fractionated coconut oil, lecithin and a mixture of the same.

Statins are drugs that lower blood cholesterol levels by inhibiting hydroxymethylglutaryl CoA (HMG-CoA) reductase. Examples of statin compounds include pitavastatin, pravastatin, simvastatin, lovastatin, atorvastatin, fluvastatin and salts thereof. In certain embodiments, statins may be from naturally occurring sources may be used. For example, a naturally occurring statins such as policosanols and gugulipids may be found in, for example, rice bran extract, wheat germ, wheat germ extract, beeswax, or red yeast rice extract.

Azetidinone-based compounds can inhibito cholesterol absorption and include, for example, ezetimibe, ezetimibe phenolic glucuronide, or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug. Two other ezetimibe related analogs and cholesterol absorption inhibitors for use in the present invention, for example, are referred to in the literature as: 1) SCH 58053 or (+)-7-(4-chlorophenyl)-2-(4-fluorophenyl)-7-hydroxy-3R-(4-hydroxyphenyl)-2-azaspiro [3,5]nonan-1-one) (see J. Lipid Res. 43:1864-1873 (2002)) and 2) SCH 48461 or (3R)-3-Phenylpropyl)-1,(4S)-bis(4-methoxyphenyl)-2-azetidinone (see J. Med. Chem., 41:973-980 (1998)).

LDL catabolism enhancers are drugs that lower blood cholesterol levels by increasing the number of LDL (low-density lipoprotein) receptors, and include, but are not limited to, the compounds described in Japanese Patent Application No. 117 (1995)-316144, which is incorporated by reference herein in its entirety.

Non-steroidal anti-inflammatory drugs (NSAIDs) may include in various formulations of the invention. In certain embodiments, the NSAID may be any of the following: ibuprofen, naproxen, ketoprofen, oxaprozin, diclofenac, indomethacin, sulindac, piroxicam, meclofenamate, mefanamic acid, nabumetone, etoldolac, ketorolac, choline magnesium trisalicylate, aspirin, diflunisal, salsalate, fenoprofen, flurbiprofen, pirprofen, tiaprofenic acid, loxoprofen, indoprofen, fenbufen, carprofen, suprofen, celecoxib, valdecoxib, rofecoxib, parecoxib, deracoxib, lumiracoxib, etoricoxib or meloxicam.

Embodiments further include nutraceuticals including the nutraceutical equivalents to any of the agents described above and one or more activated fatty acids. Thus, in certain embodiments, the nutraceuticals may include one or more activated fatty acid in combination with one or more other nutraceutical compound or one or more other secondary agent. Nutraceuticals containing various combinations of ingredients are well known in the art, and any known nutraceutical may be combined with one or more activated fatty acids to produce a combination nutraceutical. For example, in various embodiments, activated fatty acids may be combined with vitamins including vitamins A, B, including vitamin B-1, B-2, B-6, B-12, C, D including vitamin D3, and E, and the like and derivatives thereof, minerals such as selenium and the like, plant extracts such as β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, and the like, nutraceutical oils such as flaxseed oil, borage seed oil, and other know nutraceutical components such as coenzyme Q10, glucosamine derivatives, methylsulfonylmethane, pantothenic acid, biotin, thiamin, riboflavin, niacin, Colic acid, palmitic acid, and the like. Thus, without wishing to be bound by theory, nearly any nutraceutical can be incorporated into the activated fatty acid containing nutraceuticals described herein.

In particular embodiments, one or more additional ingredients may be provided to produce a nutraceutical for treating or preventing specific diseases or indication. For example, in some embodiments, activated fatty acids may be combined with other nutraceutically active components that can act as antioxidants such as vitamin C, vitamin E, vitamin D, selenium and the like to create a nutraceutical for treating aging and cancer. In other embodiments, a nutraceutical for treating or preventing diseases of the eye may be prepared by combining activated fatty acids with, for example, vitamin A and/or β-carotene, in still other embodiments, a nutraceutical with neuroprotective activities or that enhances cognitive abilities may be prepared by combining activated fatty acids with, for example, ginko biloba. In yet other embodiments, nutraceuticals for treating or preventing heart or circulatory diseases may be prepared by combining activated fatty acids with policosanol, guggulipids, rice bran extract, enzyme-treated stabilized rice bran, a solubilized fraction of rice bran oil, wheat germ, wheat germ extract, beeswax, red yeast rice extract, and or other nutraceuticals known to exhibit statin-like activity. In further embodiments, components with various activities may be combined. For example, a nutraceutical with neuroprotective activities may include one or more antioxidants such as vitamin C, vitamin E, or selenium along with ginko biloba, since it is well known that antioxidants are also effective neuroprotectants. In yet other embodiments, vitamin E may be provided to any nutraceutical described herein to stabilize the activated fatty acids and increase the shelf life of the nutracuetical.

Nutraceuticals having fatty acids and one or more additional nutraceutically active components may be combined in a single dose formulation by known methods. For example, in some embodiments, lipophilic additional nutraceutically active components may be combined with the activated fatty acids directly. In other embodiments, the activated fatty acid may be separated from a non-lipophilic additional nutraceutically active component by, for example, preparing separate cores that are combined into a single capsule or incorporating the non-lipophilic additional nutraceutically active component into one or more coating layers.

In embodiments in which activated fatty acid are combined with a secondary form of treatment, the activated fatty acid may be administered in a separate dosage unit from the secondary agent such that each treatment is provided separately. In other embodiments, the activated fatty acid may be provided in the same dosage unit as one or more secondary agent. In general, each of the one or more secondary agents may be provided in an appropriate amount based on the knowledge in the art, federal recommendations, and the like. The skilled artisan is therefore capable of determining an appropriate amount of any of the secondary active agents described above. In some exemplary embodiments, the activated fatty acid may be combined with the one or more secondary agent in a range of about 1:1000 to about 1000:1 by weight or about 200:1 to about 200:1 by weight. In other exemplary embodiments, the activated fatty acid may be present in an amount from about 1 mg to about 3000 mg or from about 10 mg to about 2000 mg, and each of the one or more secondary agents may be present in an amount from about 1 mg to about 1000 mg, about 5 mg to about 500 mg, and about 5 mg to about 100 mg. In certain embodiments, a single dosage unit may include about 500 mg to about 2000 mg or about 1000 mg of one or more activated ω-3 fatty acids, and about 1 mg to about 150 mg or about 5 mg to about 100 mg of a statin compound, about 1 mg to about 300 mg or 10 to about 100 mg of a fibrate compound or a combination thereof.

The activated fatty acids of various embodiments may be prepared by any method known in the art. For example, in particular embodiments, the activated fatty acids may be derived from natural sources such as, for example, fish oils and plant oils which may contain activated fatty acids, and in particular, nitro-fatty acids and keto-fatty acids, that can be isolated, purified or concentrated form the fish oil. In other embodiments, an activated fatty acid may be prepared by contacting an naturally occurring unsaturated fatty acids with one or more nitro containing compounds, nitrogenating agents, and/or oxygenating agents and the activated fatty acids may be isolated, purified, or concentrated from the resulting oils, and in some embodiments, such methods may be carried out in the presence of one or more cofactors and/or catalysts. For example, in certain embodiments, activated fatty acids may be prepared by combining an unsaturated fatty acid with one or more nitrogenating agents and/or oxygenating agents such as ammonia or primary amines, molecular oxygen and an oxidation catalyst as described in U.S. Pat. No. 4,599,430, which is hereby incorporated by reference in its entirety.

In some embodiments, the isolation, purification, or concentration of activated fatty acids may be accomplished using a variety of solid phase chromatographic strategics, which may be subjected to a gradient of solvent of increasing or decreasing polarity. In certain embodiments, an affinity based or covalent adduction strategy may be used. For example, in some exemplary embodiments, immobilized thiol-containing compounds or chromatographic beads can be used to concentrate activated fatty acids from natural or treated oils. In yet other embodiments, natural or treated oils or concentrated, isolated, or purified activated fatty acids may be additionally treated to remove harmful by-products and oxidized fatty acids.

The unsaturated fatty acids may be any unsaturated fatty acid known in the art. For example, in some embodiments, the unsaturated fatty acid may be pharmaceutical or nutraceutical grade fatty acids such as, for example, pharmaceutical or nutraceutical grade ω-3 fatty acids. In other embodiments, the unsaturated fatty acids may be derived from fish oils which may or may not have been obtained by fractionation fish oils to concentrate the unsaturated fatty acids. In still other embodiments, the unsaturated fatty acids may be a synthetic fatty acid manufactured by any method known in the art.

The source of the electron withdrawing group may be any compound known in the art that is capable of generating an electron withdrawing group that can be incorporated into the activated fatty acid, such as, for example, $NaNO_2$, $AgNO_2$, $HSO_2OH$, and the like. {I don't see these reactions steps above so they have been removed}

In other embodiments, an activated fatty acid may be prepared using a modified aldol condensation such as the Henry reaction. A review of the Henry reaction and methods related to the Henry method can be found, for example, in Frederick A. Luzzio, F. A. "The Henry reaction: recent examples" Tetrahedron 2001, 57, 915-945 which is hereby incorporated by reference in its entirety. Known variations of the Henry reaction may also be useful in preparing activated fatty acids and all such methods are embodied herein. For example, in some embodiments, variations of the Henry reaction including, but not limited to, the Wittig-like variation of the Henry reaction, the Horner-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Horner-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Horner-Wittig, Horner-Wadsworth-Emmons can be found, for example, in Peterson, Johnson, and Julia reactions. Blakemore, P. R. "The modified Julia olefination: alkene synthesis via the condensation of metallated heteroarylalkylsulfones with carbonyl compounds *J. Chem. Soc., Perkin Trans.* 1, 2002, 2563-2585 which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitroaldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitro-octadec-9-enoic Acids" *Organic Letters*, 2006, 8, 3931-3934 which provides one regioisomer and usually one of two possible alkene cis/trans or Z/E diastereomers, in high purity and usually in high chemical yield, which is hereby incorporated by reference in its entireties.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N. C. "Catalytic Asymmetric Henry Reaction" *Tetrahedron: Asymmetry* 2006, 17, 3315-3326 which is hereby incorporated by reference in its entirety, describes methods for preparing stereospecific isomers of nitoralkenes.

In still other embodiments, alkenes (olefins) may be prepared by metal-mediated cross coupling reactions (joining together of two molecules to make one new molecule) by condensation onto a carbonyl compound. Such methods have not been applied to the formation of nitroalkenes or to the formation of other alkenes with electron-withdrawing substituents, but such methods could be adapted to the synthesis of alkenes with electron-withdrawing substituents. For example, named cross coupling reactions such as the Heck, Suzuki and Stille coupling, along with others may be used to prepare activated fatty acids. Such methods are well known in the art. A review of such reactions of can be found in, for example, Metal-Catalyzed Cross-Coupling Reactions de Meijere, Armin/Diederich, François (eds.) Wiley-VCH, Weinheim 2004. XXII, ISBN-10: 3-527-30518-1 and ISBN-13: 978-3-527-30518-6 which are hereby incorporated by reference in their entireties.

For example, in some embodiments a solubilizer may be vitamin E or a vitamin E derivative such as, but not limited to, α-, β-, γ-, δ-, ζ1-, ζ2- and ε-tocopherols, their dl, d and l forms and their structural analogues, such as tocotrienols; the corresponding derivatives, esters, produced with organic acids; and mixtures thereof. In particular embodiments, vitamin E derivative solubilizers may include tocopherols, tocotrienols and tocopherol derivatives with organic acids such as acetic acid, propionic acid, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, polyethylene glycol succinate and salicylic acid.

In other embodiments, monohydric alcohol including, for example, ethanol, isopropanol, t-butanol, a fatty alcohol, phenol, cresol, benzyl alcohol or a cycloalkyl alcohol, or monohydric alcohol esters of organic acids such as, for example, acetic acid, propionic acid, butyric acid, a fatty acid of 6-22 carbon atoms, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid and salicylic acid may be used as solubilizers. In certain embodiments, solubilizers in this group may include trialkyl citrates such as triethyl citrate, acetyltriethyl citrate, tributyl citrate, acetyltributyl citrate and mixtures thereof; lower alcohol fatty acid esters such as ethyl oleate, ethyl linoleate, ethyl caprylate, ethyl caprate, isopropyl myristate, isopropyl palmitate and mixtures thereof and lactones ε-caprolactone, δ-valerolactone, β-butyrolactone, isomers thereof and mixtures thereof.

In still other embodiments, the solubilizer may be a nitrogen-containing solvent such as, for example, acetonitrile, dimethylformamide, dimethylacetamide, N-alkylpyrrolidone, N-hydroxyalkylpyrrolidone, N-alkylpiperidone, N-alkylcaprolactam and mixtures thereof wherein alkyl may be a $C_{1-12}$ branched or straight chain alkyl. In particular embodiments, nitrogen-containing solvents may include N-methyl 2-pyrrolidone, N-ethyl 2-pyrrolidone or a mixture thereof. Alternatively, the nitrogen-containing solvent may be in the form of a polymer such as polyvinylpyrrolidone.

In yet other embodiments, solubilizers may include phospholipids such as phosphatidylcholine, phosphatidylethanolamine, phosphatidylserine, phosphatidylinositol, lecithins, lysolecithins, lysophosphatidylcholine, polyethylene glycolated phospholipids/liysophospholipids, lecithins/lysolecithins and mixtures thereof.

In still other embodiments, glycerol acetates and acetylated glycerol fatty acid esters and glycerol fatty acid esters may be used as solubilizers. In such embodiments, glycerol acetates may include acetin, diacetin, triacetin and mixtures thereof. Acetylated glycerol fatty acid esters may include acetylated monoglycerides, acetylated diglycerides and mixtures thereof with a fatty acid component that may be about 6 to about 22 carbon atoms. Glycerol fatty acid ester may be a monoglyceride, diglyceride, triglyceride, medium chain monoglycerides with fatty acids having about 6-12 carbons, medium chain diglycerides with fatty acids having about 6-12 carbons, medium chain triglycerides with fatty acids having about 6-12 carbons and mixtures thereof.

Further embodiments include solubilizers that may be a propylene glycol esters or ethylene glycol esters. In such embodiments, propylene glycol esters may include, for example, propylene carbonate, propylene glycol monoacetate, propylene glycol diacetate, propylene glycol fatty acid esters, acetylated propylene glycol fatty acid esters and mixtures thereof. Alternatively, propylene glycol fatty acid esters may be a propylene glycol fatty acid monoester, propylene glycol fatty acid diester or mixture thereof. In certain embodiments, propylene glycol ester may be propylene glycol monocaprylate, propylene glycol dicaprylate, propylene glycol dicaprate, propylene glycol dicaprylate/dicaprate and mixtures thereof. Ethylene glycol esters may include monoethylene glycol monoacetates, diethylene glycol esters, polyethylene glycol esters, ethylene glycol monoacetates, ethylene glycol diacetates, ethylene glycol fatty acid monoesters, ethylene glycol fatty acid diesters, polyethylene glycol fatty acid monoesters, polyethylene glycol fatty acid diesters and mixtures thereof. In such embodiments, the fatty acid may have about 6 to about 22 carbon atoms.

Hydrophilic solvents that may also be utilized as solubilizers include, for example, alcohols, for example, water miscible alcohols, such as, ethanol or glycerol; glycols such as 1,2-propylene glycol; polyols such as a polyalkylene glycol, for example, polyethylene glycol. Alternatively, hydrophilic solvents may include N-alkylpyrolidones such as N-methylpyrolidone, triethylcitrate, dimethylisosorbide, caprylic acid or propylene carbonate.

The activated fatty acid containing core may be coated with one or more coating layer. For example, in some embodiments, the gel capsule may include a water-soluble gel layer between the coating layer and the activated fatty acid core. In other embodiments, the gel capsules may include a number of additional coatings on the capsules such as, for example, immediate release coatings, protective coatings, enteric or delayed release coatings, sustained release coatings, barrier coatings, and combinations thereof. In some embodiments, one or more secondary agent or non-activated fatty acid may be mixed with the activated fatty acid and/or be present in either a coating layer, a water-soluble gel layer, or an additional coating layer. Additionally, in various embodiments, the activated fatty acid and/or one or more secondary agents of the invention may be formulated with one or more additional non-pharmaceutically active ingredients including, but not limited to, solubilizers, antioxidants, chelating agents, buffers, emulsifiers, thickening agents, dispersants, and preservatives. In some embodiments, the activated fatty acids may be encapsulated in a coating prepared from gelatin as described in U.S. Pat. No. 6,531,150, which is hereby incorporated by reference in its entirety. The gelatin layer may further include one or more other non-gelatin protein and/or one or more polysaccharide such as, for example, albumin, pectin, guaran gum, carrageenan, agar and the like, and/or one or more additive such as, for example, enteric materials, plasticizers, preservatives, and the like. Enteric materials used in embodiments of the invention include any material that does not dissolve in the stomach when the gel capsule is administered orally and include, but are not limited to, pectin, alginic acid, cellulose such as carboxylmethylcellulose, celluloseacetate phthalate, and the like, Eudragit™, an acrylic copolymer. Without wishing to be bound by theory, the addition of an enteric coating may provide a means for masking the flavor of activated fatty acids by limiting the release of the activated fatty acids to the stomach. Plasticizers may include polyhydric alcohols, such as sorbitol, glycerin, polyethylene glycol and the like. In the embodiments described above, each coating layer may be from about 0.001 to about 5.00 mm or 0.01 to 1.00 mm thick.

The coatings of various embodiments may further include one or more film forming materials and/or binders and/or other conventional additives such as lubricants, fillers, antiadherents, antioxidants, buffers, solubilizers, dyes, chelating agents, disintegrants, and/or absorption enhancers. Surfactants may act as both solubilizers and absorption enhancers. Additionally, coatings may be formulated for immediate release, delayed or enteric release, or sustained release in accordance with methods well known in the art. Conventional coating techniques are described, e.g., in Remington's Pharmaceutical Sciences, 18th Ed. (1990), hereby incorporated by reference. Additional coatings to be employed in accordance with the invention may include, but are not limited to, for example, one or more immediate release coatings, protective coatings, enteric or delayed release coatings, sustained release coatings, barrier coatings, and combinations thereof. In some embodiments, an immediate release coating may be used to improve product elegance as well as for a moisture barrier, and taste and odor masking. Rapid breakdown of the film in gastric media is important, leading to effective disintegration and dissolution.

Capsular materials (i.e., the activated fatty acid containing core and/or one or more coating layers) may further include one or more preservatives, coloring and opacifying agents, flavorings and sweeteners, sugars, gastroresistant substances, or combinations thereof. Suitable preservative and colorant are known in the art and include, for example, benzoic acid, para-oxybenzoate, caramel colorant, gardenia colorant, carotene colorant, tar colorant and the like. In particular embodiments, one or more flavoring agents may be included the contents of the core of the gelatin capsule or in one or more coating layers of the capsule, or a combination thereof. For example, providing a palatable flavoring to the activated fatty acid gel capsule may be achieved by providing a flavored coating layer having a water soluble flavor. In such embodiments, from about 0.25% and about 1.50% by weight of said coating layer may be the water soluble flavoring. Any suitable flavor known in the art may be provided to the coating layer, such as, berry, strawberry, chocolate, cocoa, vanilla, lemon, nut, almond, cashew, macadamia nut, coconut, blueberry, blackberry, raspberry, peach, lemon, lime, mint, peppermint, orange, banana, chili pepper, pepper, cinnamon, and pineapple. In some embodiments, an oil soluble flavoring may be mixed with a activated fatty acid core that is encapsulated within the capsule. In such embodiments, from about 0.25% and about 1.50% by weight of said core may be the oil soluble flavoring. Such oil soluble flavoring may be similar to the taste of the flavor of the capsule, e.g., strawberry and strawberry, or the taste of the oil flavoring may be complementary to the capsule flavoring, e.g., banana and strawberry. Such flavoring agents and methods for providing flavoring to fatty acid containing capsules may be found in U.S. Pat. Nos. 6,346,231 and 6,652,879 which are hereby incorporated by reference in their entireties.

In some embodiments, the gel capsules of embodiments may include at least one coating layer including one or more secondary agent. In such embodiments, a layer including one or more secondary agent may be of sufficient thickness to prevent oxidative degradation of the one or more secondary agent. For example, in some embodiments, the thickness of this layer may be from about 5 to about 400 microns, about 10 to about 200 microns, about 20 to about 100 microns, or in certain embodiments, from about 40 to about 80 microns. In other embodiments, the thickness of such layers may be expressed in terms of percentage weight gain based on the total weight of the capsule. For example, a layer including one or more secondary agents may create a weight gain of about 0.05 to about 20%, about 0.1 to about 10%, about 0.1 to about 5%, and in particular embodiments about 0.25 to about 1%. In certain embodiments, a coating layer containing one or more secondary agent may further include at least one compound to prevent oxidative degradation. For example, in some embodiments, at least one polymer, such as, but not limited to cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions and combinations thereof, preferably hydroxypropyl cellulose, ethyl cellulose, and mixtures thereof, may be added to the coating layer at a ratio of polymer to secondary agent of from about 1:20 to about 20:1 by weight or about 1:5 to about 10:1 by weight. In particular, where the amount of secondary agent is less than about 15 mg, the amount of polymer may be from about 1:2 to about 5:1 or from about 1:1 to about 4:1, and in embodiments where the amount of secondary agent is about 15 mg or more, the amount of polymer may be from about 1:4 to about 4:1 or about 1:3 to about 2:1.

In embodiments in which one or more secondary agents are applied in a coating layer, the secondary agent may be provided as a homogenous coating solution or a heterologous suspension in a pharmaceutically acceptable solvent. Such pharmaceutically acceptable solvents may be an aqueous or organic solvent such as, for example, methanol, ethanol, isopropranol, ethylene glycol, acetone, or mixtures thereof. In other embodiments, pharmaceutically acceptable solvents may include, but are not limited to, polypropylene glycol; polypropylene glycol; polyethylene glycol, for example, polyethylene glycol 600, polyethylene glycol 900, polyethylene glycol 540, polyethylene glycol 1450, polyethylene glycol 6000, polyethylene glycol 8000, and the like; pharmaceutically acceptable alcohols that are liquids at about room temperature, for example, propylene glycol, ethanol, 2-(2-ethoxyethoxy)ethanol, benzyl alcohol, glycerol, polyethylene glycol 200, polyethylene glycol 300, polyethylene glycol 400 and the like; polyoxyethylene castor oil derivatives, for example, polyoxyethyleneglycerol triricinoleate or polyoxyl 35 castor oil, polyoxyethyleneglycerol oxystearate, RH 40 (polyethyleneglycol 40 hydrogenated castor oil) or RH 60 (polyethyleneglycol 60 hydrogenated castor oil), and the like; saturated polyglycolized glycerides; polyoxyethylene alkyl ethers, for example, cetomacrogol 1000 and the like; polyoxyethylene stearates, for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like; ethyl oleate, isopropyl palmitate, isopropyl myristate and the like; dimethyl isosorbide; N-methylpyrrolidinone; paraffin; cholesterol; lecithin; suppository bases; pharmaceutically acceptable waxes, for example, carnauba wax, yellow wax, white wax, microcrystalline wax, emulsifying wax and the like; pharmaceutically acceptable silicon fluids; soribitan fatty acid esters such as sorbitan laurate, sorbitan oleate, sorbitan palmitate, sorbitan stearate and the like; pharmaceutically acceptable saturated fats or pharmaceutically acceptable saturated oils, for example, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate and the like.

Any method for preparing gel capsules known in the art may by used in various embodiments of the invention. For example, in one embodiment, capsules may be produced by a method including the steps of preparing a sheet of an outer coating layer and one or more sheets of other layers, laminating the sheets, drying the laminated sheets to obtain a dried sheet, and encapsulating one or more activated fatty acid or one or more activated fatty acids and one or more secondary agents within the dried sheet on a rotary filler to form a seamed capsule. In another embodiment, seamless capsules may be produced using an instrument equipped with two or more nozzles arranged concentrically. In other embodiments, gelatin capsules may be manufactured as, for example, a two-piece, sealed or unsealed hard gelatin capsule.

In another embodiment, a gelatin capsule including nitro fatty acids may be formed by the encapsulation of a dose of one or more nitro fatty acid in a gelatin capsule. In such embodiments, the gelatin capsule may be made of, for example, gelatin, glycerol, water, a flavoring, a coloring agent and combinations thereof, and the nitro fatty acid dose may be, for example, 180 mg of nitrated DHA and 60 mg of nitrated EPA. The manufacturing process of such embodiments may include the steps of combining gelswatch ingredients, melting and forming a liquefied gelswatch, delivering the liquefied gelswatch and the nitro fatty acid to an encapsulation machine, encapsulating a dose of nitro fatty acid, drying the encapsulated dose, washing the encapsulated dose and packaging the nitro fatty acid capsules for shipment. The gelswatch ingredients may include any ingredients described herein that are useful in the production of gelatin capsules such as, for example, gelatin or a gelatin substitute such as modified starch or other suitable gelatin substitute known in the art, a softener such as glycerol or sorbitol or other suitable polyol or other gelatin softener known in the art, a flavoring agent such as strawberry flavor Firmenich #52311A or other suitable gelatin capsule flavoring known in the art and optionally a coloring agent such as keratin or other suitable gelatin capsule coloring agent known in the art.

In particular embodiments, the gel capsule may be formed from a gelswatch mixture of about 45 parts by weight of gelatin, about 20 parts by weight of glycerol, about 35 parts by weight of water and about 0.5 or more parts by weight of flavoring. The gelswatch ingredients may be heated to about 60° C. to 70° C. and mixed together to form liquefied gelswatch. The liquefied gelswatch and the nitro fatty acid may then be poured into an encapsulation machine. The encapsulation machine then forms the nitro fatty acid capsule by encapsulating the nitro fatty acid dose into a gelatin capsule.

The capsule can then be dried at a temperature of, for example, about 20° C. The water content of the capsule may be reduced by evaporation during the drying step. The capsule can then be washed and ready for packaging, selling, or shipping. In some embodiments, a sweetener or flavoring agent can be added to the capsule through a dipping process. In the dipping process, the gelatin capsule is dipped in a sweetener/flavoring solution and then dried, allowing for the sweetener to form a coating around the outside of the capsule. In some embodiments, a sweetener or flavoring agent may be added to the capsule through an enteric coating process, and in other embodiments, a liquefied sweetener or flavoring agent can be sprayed on to the outside of the gelatin capsule and dried. Other methods of making gelatin capsules are known in the art and contemplated.

In various embodiments, the one or more coatings on the capsule may be applied by any technique known in the art including, but not limited to, pan coating, fluid bed coating or spray coating, and the one or more coatings may be applied, for example, as a solution, suspension, spray, dust or powder. For example, in some embodiments, a polymeric coating may be applied as aqueous-based solutions, organic-based solutions or dispersions containing and, in some embodiments, one or more secondary agent. In such embodiments, polymer-containing droplets may atomized with air or an inert gas and sprayed onto the core containing the activated fatty acids, and in some embodiments, heated air or inert gas may be added to facilitate evaporation of the solvent and film formation. In the case of soft gelatin capsules, the processing parameters of spray rate and bed temperature must be controlled to limit solubilization and capsule agglomeration. Additionally, a high bed temperature may result in evaporation of residual water from the capsule shell, causing the capsule to become brittle. In addition, coating uniformity which includes mass variance of the coated capsules and variance of the content of the coated activated fatty acid and accuracy of deposition must be evaluated.

Gel capsules of various embodiments of the invention may be of any shape such as, but not limited to, round, oval, tubular, oblong, twist off, or a non-standard shape (e.g., animal, tree, star, heart, etc.), and the size of the capsule may vary in accordance to the volume of the fill composition intended to be contained therein. For example, in some embodiments, hard or soft gelatin capsules may be manufactured using conventional methods as a single body unit comprising the standard capsule shape. A single-body soft gelatin capsule typically may be provided, for example, in sizes from 3 to 22 minims (1 minim=0.0616 ml) and in shapes of oval, oblong or others. Similarly, hard gel capsules may be manufactured using conventional methods in standard shapes and various standard sizes, such as those designated (000), (00), (0), (1), (2), (3), (4), and (5) where the largest number corresponds to the smallest size. Non-standard shapes may be used as well.

Other pharmaceutical formulations containing the compounds of the invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of an activated fatty acid in solid dosage form may vary. For example, in one embodiment, a liquid or gelatin formulation of the activated fatty acid may be prepared by combining the activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an activated fatty acid prepared as described above may be lyophilized to a solid that may be mixed with one or more pharmaceutically acceptable excipient, carrier or diluent to form a tablet, and in yet another embodiment, the activated fatty acid of an oily preparation may be crystallized to from a solid which may be combined with a pharmaceutically acceptable excipient, carrier or diluent to form a tablet.

Further embodiments which may be useful for oral administration of activated Catty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyeeroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH$_2$—CH$_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include activated fatty acids administered in combination with other active ingredients such as, for example, adjuvants, protease inhibitors, or other compatible drugs or compounds where such combination is seen to be desirable or advantageous in achieving the desired effects of the methods described herein.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects or the present invention will be illustrated with reference to the following non-limiting examples.

Examples 1-9

Exemplary gel capsules may be prepared as described above including the ingredients listed in Table 1.

| Compound | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| EPA[1] | 0 | 0 | 200 | 100 | 0 | 0 | 0 | 100 | 100 |
| DHA[2] | 400 | 400 | 200 | 300 | 180 | 360 | 14 | 100 | 100 |
| NO-OLA[3] | 0 | 200 | 100 | 0 | 0 | 0 | 0 | 0 | 400 |
| NO-LNA[4] | 200 | 0 | 100 | 200 | 120 | 240 | 200 | 400 | 0 |
| Vitamin E | 3.0 | 3.0 | 3.0 | 3.0 | 2.3 | 0 | 0 | 3.0 | 3.0 |
| Flavoring | | | | | 1.0 | 1.0 | 2.0 | 1.0 | 1.0 |

[1]EPA-eicosapentaenoic acid
[2]MA-docosahexaenoic acid
[3]OLA-oleic acid
[4]LNA-linoleic acid Example 10-20

Exemplary gel capsules may be prepared as described above including the ingredients listed in Table 2.

| Compound | Ex. 10 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| EPA[1] | 200 | 200 | 200 | 200 | 200 | 200 | 200 | 200 | 200 | 200 |
| DHA[2] | 200 | 200 | 200 | 200 | 200 | 200 | 200 | 200 | 200 | 200 |
| NO-OLA[3] | 100 | 100 | 100 | 100 | 100 | 100 | 100 | 100 | 100 | 100 |
| NO-LNA[4] | 100 | 100 | 100 | 100 | 100 | 100 | 100 | 100 | 100 | 100 |
| Vitamin E | 3 | 3 | 3 | 3 | 0 | 0 | 0 | 0 | 0 | 0 |
| Vitamin B12 | 20 | 20 | 0 | 0 | 20 | 20 | 0 | 0 | 0 | 20 |
| Folic Acid | 0 | 0.8 | 0 | 0 | 0 | 0.8 | 0 | 0 | 0 | 0.8 |
| Ginko Biloba | 0 | 0 | 400 | 0 | 0 | 0 | 400 | 0 | 400 | 400 |
| Ginseng | 0 | 0 | 0 | 200 | 0 | 0 | 0 | 200 | 200 | 200 |
| Flavoring | 2.0 | 2.0 | 2.0 | 2.0 | 2.0 | 2.0 | 2.0 | 2.0 | 2.0 | 2.0 |

[1]EPA-eicosapentaenoic acid
[2]DHA-docosahexaenoic acid
[3]OLA-oleic acid
[4]LNA-linoleic acid Example 21

A gel capsule nutraceutical may be prepared including: 150 mg Borage oil, 30 mg nitrated gamma linolenic acid, 1,000 mg fish body oil, 180 mg nitrated DHA, 120 mg EPA, 5 mg rosemary extract, 20 mg lemon flavor, 5 IU vitamin E, and 5 mcg Coenzyme Q-10.

Example 22

A gel capsule nutraceutical may be prepared including: 150 mg Borage oil, 30 mg nitrated gamma linolenic acid, 75 mg oleic acid, 75 mg olive oil, 25 mg liquid soy lecithin, 133 mg phytosterol ester, 400 mg fish body oil, 72 mg nitrated EPA, 48 mg nitrated DHA, 12 mg DHA, 33 IU vitamin E, 0.5 mg palm oil, 0.5 mg raspberry oil, 0.5 mg cranberry oil, 8.5 mg rice bran oil, 1.7 mg tocotrienols, 20 mg Coenzyme Q-10, and 10 mg natural lemon flavor.

Example 23

A gel capsule nutraceutical may be prepared including: 150 mg Borage oil, 30 mg nitrated gamma linolenic acid, 75 mg oleic acid, 75 mg olive oil, 25 mg liquid soy lecithin, 133 mg phytosterol ester, 400 mg fish body oil, 72 mg nitrated EPA, 48 mg nitrated DHA, 12 mg DHA, 33 IU vitamin E, 400 mg Ginko Bilbo, 8.5 mg green tea extract, 0.5 mg palm oil, 0.5 mg raspberry oil, 0.5 mg cranberry oil, 1.7 mg tocotrienols, 20 mg Coenzyme Q-10, and 10 mg natural lemon flavor.

Example 24

A gel capsule nutraceutical may be prepared including: 150 mg Borage oil, 30 mg nitrated gamma linolenic acid, 75 mg oleic acid, 75 mg olive oil, 25 mg liquid soy lecithin, 133 mg phytosterol ester, 400 mg fish body oil, 72 mg nitrated EPA, 48 mg nitrated DHA, 12 mg DHA, 33 IU vitamin E, 400 mg Ginko Bilbo, 20 mg Vitamin B12, 0.8 mg Folic Acid, 0.5 mg palm oil, 0.5 mg raspberry oil, 0.5 mg cranberry oil, 8.5 mg rice bran oil, 1.7 mg tocotrienols, 20 mg Coenzyme Q-10, and 10 mg natural lemon flavor.

Example 25

Abeta oligomer preparations: Human amyloid peptide 1-42 was obtained from a variety of commercial sources, with lot-choice contingent upon quality control analysis. Abeta 1-42 oligomers made according to published methods or isolated from human brain tissue served as positive controls. Toxicity was monitored in each image-based assay via quantification of nuclear morphology visualized with the DNA binding dye DAPI. Nuclei that were fragmented were considered to be in late stage apoptosis. Peptide lots producing unusual peptide size ranges or significant toxicity at standard concentrations on neurons were rejected.

Image Processing: Images are captured and analyzed with the Cellomics VTI automated microscope platform. For statistical analysis, a Tukey-Kramer pair-wise comparison with unequal variance is used.

A primary neuron-based functional screening assay to detect small molecule Abeta oligomer blockers: Primary rat neurons grown for at least 3 weeks in vitro were chosen as the basis for this screening assay. These neurons express the full complement of synaptic proteins characteristic of neurons in the mature brain, and exhibit a complex network of activity-dependent electrical signaling. Neurons and glia in such cultures have molecular signaling networks exhibiting excellent registration with intact brain circuitry, and for this reason have been used for over two decades as a model system for learning and memory. More complex systems such as acute or organotypic brain slices are very useful but not amenable to high throughput screening. Immortalized or transformed neuronal cell lines are amenable to high throughput screening, but do not replicate the electrophysiological state-dependent signaling of primary neuronal cultures and are unlikely to adequately model the subtle alterations in this signaling that are caused by oligomers during the earliest manifestations of the disease state. For this reason, primary neuronal cultures were chosen because of their ability to be used in high throughput screens and fidelity to what occurs in vivo.

Since synaptic and memory deficits, and not widespread cell death, predominates at the earliest stages of Alzheimer's Disease, assays that measure these changes can be used to discover small molecule inhibitors of oligomer activity. An MTT assay, can be used as a measure of toxicity in cultures.

Evidence suggests that Abeta oligomer-mediated reduction in neuronal surface receptor expression mediated by membrane trafficking are the basis for oligomer inhibition of electrophysiological measures of synaptic plasticity (LTP) and thus learning and memory. Measuring membrane trafficking rate changes induced by oligomers via formazan morphological shifts has been used in cell lines to discover Abeta oligomer-blocking drugs.

Yellow tetrazolium salts are endocytosed by cells and reduced to insoluble purple formazan in the endosomal pathway. The level of purple formazan is a reflection of the number of actively metabolizing cells in culture, and reduction in the amount of formazan was taken as a measure of cell death or metabolic toxicity in culture as well as an indicator of membrane trafficking The exocytosis assay was adapted for use with mature primary neuronal cultures grown for 3 weeks in vitro. Abeta oligomers caused a dose-dependent decrease in the amount of intracellular vesicles (puncta) filled with reduced purple formazan (FIG. 1A and FIG. 1B, circle) as measured via image processing using a Cellomics VII automated microscopy system. Several compounds were tested that have been reported to block the effects of Abeta oligomers, including the sugar alcohol scyllo-inositol (AZD-103), the nAChR antagonist hexamethonium bromide, and the NMDAR antagonists MK-801 and none were active.

Figure 1B:
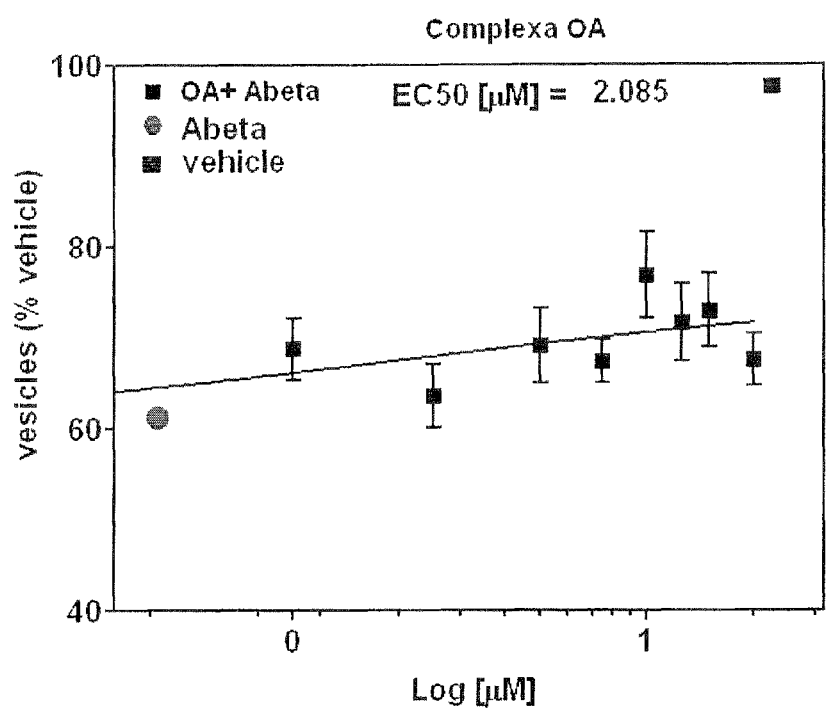
FIG. 1B shows a plot of exemplary data from an exocytosis assay performed on mature primary neuronal cultures grown for 3 weeks in vitro and shows a dose-dependent decrease in amyloid beta (Abeta) in intracellular vesicles resulting from administration of nitro-oleic acid.

Compounds were considered active if they significantly block Abeta-mediated changes in membrane trafficking, but do not significantly affect membrane trafficking when dosed on their own. An example is shown in FIG. 1B; oleic acid (Complexa OA) inhibits oligomer effects on membrane trafficking with an EC50 of 2.085 µM. Nitro-oleic acid (BAF04) appeared to have less effect on this particular assay and demonstrated little statistically relevant effect on membrane trafficking.

Modified fatty acids modified in accordance with the present invention are central nervous system drug candidates for the treatment of cognitive decline and, more particularly, Alzheimer's disease are provided. Methods of treating, inhibiting, and/or abatement of cognitive decline and Alzheimer's disease with a derivative of fatty acids are also provided. Cognitive decline, such as memory loss, confusion, impaired judgment, personality changes, disorientation, and loss of language skills occurs in much of the population as they age, in varying degree. The most common, severe and irreversible form of cognitive decline is Alzheimer's disease, which, at present, is always fatal.

As an alternative to the measure of the modified fatty acid in vitro and in viro assays described herein it is contemplated that the compounds and compositions of the present invention will show activity in memory improvements especially in an age dependent fashion. The modified fatty acids of the present invention, particularly modified DHA (e.g. N0-DHA, nitro Oleic Acid or nitro linoleic are preferred for this purpose) will show activity in memory improvements. We would expect the compositions of the present invention to show similar or greater activity than DHA in such a test. Preferably nitro linoleic and nitro oleic, and most preferably nitro oleic in this regard.

According to one embodiment of the invention, compounds derived from fish oil, preferably Omega 3s are provided. The compounds are expected activity in a beta-secretase assay and are potentially useful for the inhibition, treatment, and abatement of cognitive decline and Alzheimer's disease. The compounds and methods described herein may be used to treat one or more symptoms of cognitive decline and/or Alzheimer's disease such as memory loss, confusion, impaired judgment, personality changes, disorientation, and loss of language skills. Further, the compounds and methods described herein may be useful in inhibiting, treating, and/or abating cognitive decline and/or Alzheimer's disease by restoring long term potentiation, and/or inhibiting, treating, or abatement of one or both of neurodegeneration and general amyloidosis, more specifically, by inhibiting, treating, or abatement of one or more of amyloid production, amyloid assembly, amyloid aggregation, amyloid oligomer binding, and amyloid deposition.

In another embodiment, the invention comprises a method of inhibiting, treating, or abatement of cognitive decline and/ or Alzheimer's disease comprising the administration of a compound according to embodiments of the present invention.

The present invention provides a method of inhibiting, treating, or abatement of cognitive decline, comprising administering an activated fatty acid (e.g. $NO_2$-DIIA or $NO_2$—OA), i.e., a mammal. The compounds of the present invention are potentially useful as a therapeutic agent for the treatment of the symptoms of cognitive decline, such as memory loss, confusion, impaired judgment, personality changes, disorientation, or loss of language skills, by, for example, inhibiting, treating, or the abatement of one or more of amyloid production, amyloid aggregation, and amyloid deposition. In addition, the compounds of the present invention may be used for inhibiting, treating, or abatement of neurodegeneration and general amyloidosis, and may be used for treating, and/or the abatement of cognitive decline such as by the restoration of long term potentiation.

Example 27

Recent studies have shown that nitro-arachidonic acid can have protective effects compared with native arachidonic acid in an in vitro model of ALS. This model is based on astrocyte-induced motoneuron toxicity induced by a mutation in CuZn SOD (SOD1).

Briefly, motor neuron astrocytes cocultures were made. Cultures of wild-type motor neurons were cultured with either wild type or mutated astrocytes nitro-arachidonic acid was incubated for 24 hours with wild type motor neurons. the nitro-fatty acid limited motorneuron death caused by co-culture with astrocytes derived from transgenic mice containing a mutation in SOD1 (SOD G93A).

Figure 2:
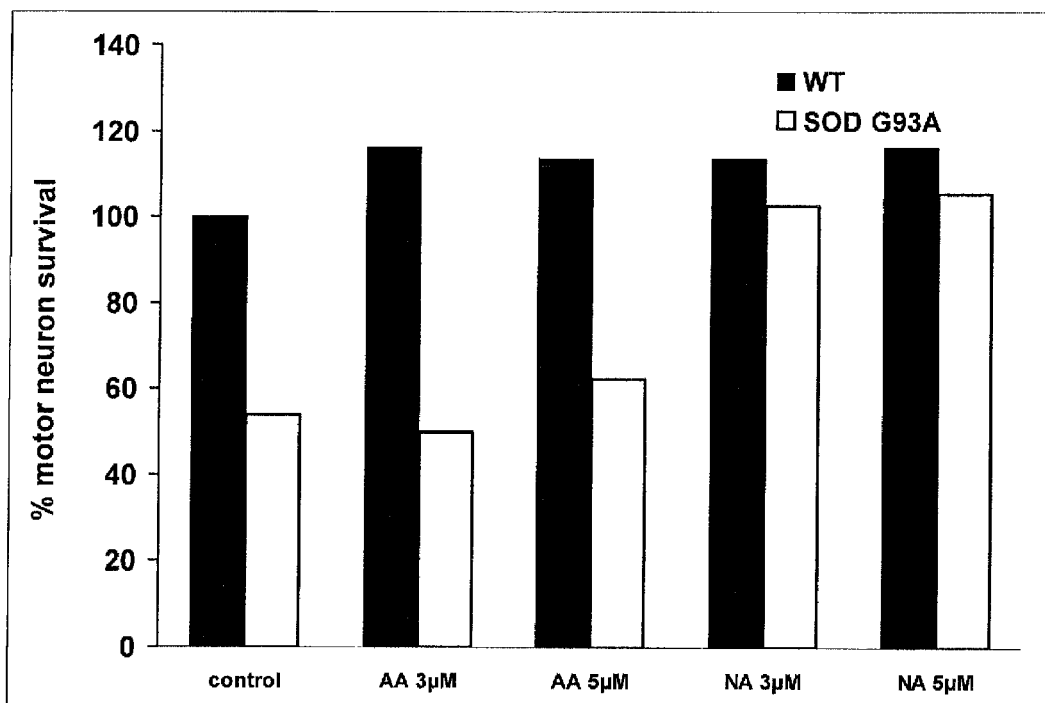
FIG. 2 is a bar graph showing motor neuron survival when oleic acid is administered.

FIG. 2 illustrates the results of these experiments. Native arachidonic acid (AA) at 3 µM and 5 µM had no effect on the motor neuron survival compared with control. 3 µM and 5 µM nitro-arachidonic acid (NA) inhibited mutant astrocyte induced motor neuron death. These results suggest that nitro-fatty acids may be able to inhibit or slow progression of motor-neuron death in ALS.

Although the present invention has been described in considerable detail with reference to certain preferred versions thereof, other versions are possible. Therefore, the spirit and scope of the invention should not be limited to the description of the preferred versions described herein.

All references cited in this disclosure are incorporated herein by reference in their entirety to the extent they support or otherwise enhance the present invention.

What is claimed is:

1. A dietary supplement comprising:
   at least one activated fatty acid;
   at least one secondary agent comprising ginko biloba, coenzyme Q10, vinpocetine, dimethylaminoethanol (DMAE), acetyl-L-carnitine, citicoline, huperzine-A, lemon balm, phosphatidylserine, saffron, tumeric, ginseng, panax ginseng, green tea extract or a combination thereof; and
   a nutraceutically acceptable carrier, excipient, or combination thereof.

2. The dietary supplement of claim 1, wherein the activated fatty acid is made from an omega-3 fatty acid, an omega-6 fatty acid, an omega-9 fatty acid, or combinations thereof.

3. The dietary supplement of claim 1, wherein the activated fatty acid is a nitro-fatty acid or a keto-fatty acid.

4. The dietary supplement of claim 1, wherein the activated fatty acid is nitro-linoleic acid, nitro-α-linoleic acid, nitro-γ-linoleic acid, nitro-oleic acid, nitro-eicosapentaenoic acid, nitro-docosahexaenoic acid, conjugated-linoleic acid, keto-linoleic acid, keto-α-linoleic acid, keto-γ-linoleic acid, keto-oleic acid, keto-eicosapentaenoic acid, keto-docosahexaenoic acid or a combination thereof.

5. The dietary supplement of claim 1, further comprising one or more of linoleic acid, α-linoleic acid, γ-linoleic acid, oleic acid, eicosapentaenoic acid (EPA), and docosahexaenoic acid (DHA).

6. The dietary supplement of claim 1, further comprising one or more nutraceuticals selected from the group consisting of vitamin A, vitamin C, vitamin D, vitamin D3, vitamin E, vitamin B, vitamin B-1, vitamin B-2, vitamin B-6, vitamin B-12, zinc, folic acid, selenium, β-carotene, goldenseal, valerian, echinacea, grape seed extracts, ephedra, yucca concentrates, rice bran extract, wheat germ, wheat germ extract, beeswax, red yeast rice extract, stevia leaf extract, flaxseed oil, borage seed oil, glucosamine derivatives, methylsulfonylmethane, pantothenic acid, biotin, thiamin, riboflavin, niacin, palmitic acid, and caffeine.

7. The dietary supplement of claim 1, wherein the at least one activated fatty acid comprises more than one activated fatty acid.

8. The dietary supplement of claim 7, wherein the fatty acid component further comprises nitro-linoleic acid, keto-linoleic acid, nitro-oleic acid, and keto-oleic acid; a second fatty acid component having one or more non-activated fatty acid selected from linoleic acid, conjugated-linoleic acid, α-linoleic acid, γ-linoleic acid, oleic acid, eicosapentaenoic acid (EPA), and docosahexaenoic acid (DHA).

9. The dietary supplement of claim 1, wherein the dietary supplement is administered to provide neuroprotection.

* * * * *